United States Patent
Yazdan Panah et al.

(10) Patent No.: US 11,525,158 B2
(45) Date of Patent: Dec. 13, 2022

(54) LINEAR DOUBLE STRANDED DNA COUPLED TO A SINGLE SUPPORT OR A TAG AND METHODS FOR PRODUCING SAID LINEAR DOUBLE STRANDED DNA

(71) Applicant: CureVac SE, Tübingen (DE)

(72) Inventors: Benyamin Yazdan Panah, Tübingen (DE); Tilmann Roos, Tübingen (DE); Veronika Wagner, Tübingen (DE); Carola Pongratz, Tübingen (DE)

(73) Assignee: CureVac SE, Tübingen (DE)

( * ) Notice: Subject to any disclaimer, the term of this patent is extended or adjusted under 35 U.S.C. 154(b) by 0 days.

(21) Appl. No.: 16/956,609

(22) PCT Filed: Dec. 21, 2018

(86) PCT No.: PCT/EP2018/086684
§ 371 (c)(1),
(2) Date: Jun. 21, 2020

(87) PCT Pub. No.: WO2019/122371
PCT Pub. Date: Jun. 27, 2019

(65) Prior Publication Data
US 2020/0392572 A1 Dec. 17, 2020

(30) Foreign Application Priority Data
Dec. 21, 2017 (WO) .................. PCT/EP2017/084264

(51) Int. Cl.
*C12Q 1/6865* (2018.01)
*C12Q 1/6806* (2018.01)

(52) U.S. Cl.
CPC ......... *C12Q 1/6865* (2013.01); *C12Q 1/6806* (2013.01); *C12Q 2520/00* (2013.01); *C12Q 2531/113* (2013.01)

(58) Field of Classification Search
CPC ............ C12Q 2525/143; C12Q 1/3865; C12Q 2525/117; C12Q 1/6806; C12Q 2565/514; C12Q 2521/307; C12Q 2520/00; C12Q 2531/113
See application file for complete search history.

(56) References Cited

U.S. PATENT DOCUMENTS

| | | | |
|---|---|---|---|
| 5,700,667 A * | 12/1997 | Marble | ................... C12P 19/34 435/91.3 |
| 2005/0032730 A1 | 2/2005 | von der Mülbe et al. | |
| 2005/0059624 A1 | 3/2005 | Hoerr et al. | |
| 2005/0250723 A1 | 11/2005 | Hoerr et al. | |
| 2006/0188490 A1 | 8/2006 | Hoerr et al. | |
| 2007/0065864 A1 | 3/2007 | Korzheva et al. | |
| 2008/0025944 A1 | 1/2008 | Hoerr et al. | |
| 2008/0194416 A1 | 8/2008 | Chen | |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |
| 2011/0053829 A1 | 3/2011 | Baumhof et al. | |
| 2011/0250225 A1 | 10/2011 | Fotin-Mleczek et al. | |
| 2012/0021043 A1 | 1/2012 | Kramps et al. | |
| 2012/0258046 A1 | 10/2012 | Mutzke | |
| 2013/0129754 A1 | 5/2013 | Thess et al. | |
| 2013/0142818 A1 | 6/2013 | Baumhof et al. | |
| 2013/0259879 A1 | 10/2013 | Baumhof et al. | |
| 2013/0280283 A1 | 10/2013 | Lorenz et al. | |
| 2013/0295043 A1 | 11/2013 | Kallen et al. | |
| 2013/0336998 A1 | 12/2013 | Kallen et al. | |
| 2015/0037326 A1 | 2/2015 | Butler-Ransohoff et al. | |
| 2015/0050302 A1 | 2/2015 | Thess | |
| 2015/0057340 A1 | 2/2015 | Thess et al. | |
| 2015/0093413 A1 | 4/2015 | Thess et al. | |
| 2015/0118183 A1 | 4/2015 | Baumhof | |
| 2015/0118264 A1 | 4/2015 | Baumhof et al. | |
| 2015/0165006 A1 | 6/2015 | Thess et al. | |
| 2015/0184195 A1 | 7/2015 | Thess et al. | |
| 2015/0218554 A1 | 8/2015 | Thess | |
| 2015/0306249 A1 | 10/2015 | Baumhof et al. | |
| 2015/0320847 A1 | 11/2015 | Thess et al. | |

(Continued)

FOREIGN PATENT DOCUMENTS

WO   WO-2017109161 A1 * 6/2017 ............. C12N 15/10
WO   WO 2018/172556      9/2018

(Continued)

OTHER PUBLICATIONS

Agnew et al., "Iterative In Situ Click Chemistry Creates Antibody-like Protein-Capture Agents," Angew. Chem. Int. Ed., vol. 48, pp. 4944-4948. (Year: 2009).*
Ren et al., "Azide and trans-cyclootene dUTPs: incorporation into DNA probes and fluorescent click-labeling," Analyst, vol. 140, pp. 2671-2678. (Year: 2015).*
Fujita et al., "Surprising liability of biotin-streptavidin bond during transcription of biotinylated DNA bound to paramagnetic streptavidin beads," *Biotechniques Rapid Dispatches*, 14(4):608-617, 1993.
PCT International Search Report and Written Opinion issued in International Application No. PCT/EP2018/086684, dated Feb. 12, 2019.

*Primary Examiner* — Young J Kim
(74) *Attorney, Agent, or Firm* — Parker Highlander PLLC

(57) ABSTRACT

The present invention is concerned with linear double stranded DNA, which is coupled to a single support or a tag at the 3' end of its non-coding strand and methods for producing said linear double stranded DNA. The present invention further relates to the use of said linear double stranded DNA in an RNA in vitro transcription reaction and also to a method for producing RNA in vitro. The present invention also relates to a bioreactor for RNA in vitro transcription.

19 Claims, 11 Drawing Sheets

Specification includes a Sequence Listing.

(56) References Cited

U.S. PATENT DOCUMENTS

| | | |
|---|---|---|
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |

FOREIGN PATENT DOCUMENTS

| | | |
|---|---|---|
| WO | WO 2018/211038 | 11/2018 |
| WO | WO 2019/077001 | 4/2019 |
| WO | WO 2019/092153 | 5/2019 |
| WO | WO 2019/193183 | 10/2019 |
| WO | WO 2020/002525 | 1/2020 |
| WO | WO 2020/002598 | 1/2020 |
| WO | WO 2020/123300 | 6/2020 |
| WO | WO 2020/127959 | 6/2020 |
| WO | WO 2020/128031 | 6/2020 |
| WO | WO 2020/161342 | 8/2020 |
| WO | WO 2021/156267 | 8/2021 |

\* cited by examiner

LINEAR DOUBLE STRANDED DNA COUPLED TO A SINGLE SUPPORT OR A TAG AND METHODS FOR PRODUCING SAID LINEAR DOUBLE STRANDED DNA

This application is a national phase application under 35 U.S.C. § 371 of International Application No. PCT/EP2018/086684, filed Dec. 21, 2018, which claims benefit of International Application No. PCT/EP2017/084264, filed Dec. 21, 2017, the entire contents of each of which are hereby incorporated by reference.

FIELD OF THE INVENTION

The present invention relates to a linear double stranded DNA comprising a coding sequence element, which is coupled at the 3' end of its non-coding strand to a support or a tag and wherein said support or tag is the only support or tag coupled to said DNA.

The present invention further relates to methods for producing the above described linear double stranded DNA. A couple of methods include the steps of adding a modified deoxynucleotide to the 3' ends of linear double stranded DNA and coupling said modified deoxynucleotide to a support or tag. Digestion of the obtained linear double stranded DNA by an endonuclease leads to linear double stranded DNA which comprises a support or a tag only at the 3' end of its non-coding strand. Another method comprises the addition of a tag-linked deoxynucleotide to the 3' end of each strand of linear double stranded DNA followed by endonuclease restriction in order to obtain linear double stranded DNA with a single tag at the 3' end of the non-coding strand. A further method comprises specifically adding a modified deoxynucleotide to the 3' end of the non-coding strand at a blunt end of a linear double stranded DNA with a blunt and a sticky end and further comprises coupling said DNA via said modified deoxynucleotide to a support or a tag. Specific addition to the 3' end of the non-coding strand as described above can also be obtained with a tag-linked deoxynucleotide, Kits comprising essential components for performing the afore-mentioned methods are provided by the present invention.

The use of the linear double stranded DNA comprising a coding sequence element and a support or tag at the 3' end of its non-coding strand for RNA in vitro transcription is also part of the present invention. Furthermore, also a method for producing RNA in vitro comprising providing the double stranded linear DNA as described above as template DNA is part of the present invention. Additionally, the present invention relates to a bioreactor for RNA in vitro transcription comprising the linear double stranded DNA as described above.

BACKGROUND OF THE INVENTION

RNA-based therapy is one of the most promising and quickly developing fields of modern medicine and ribonucleic acid molecules (RNA) therefore represent an emerging class of drugs. RNA-based therapeutics provide highly specific and individual treatment options for the therapy of various diseases and may for instance be used in immunotherapy, gene therapy and genetic vaccination. Therefore, there is a need for producing high-quality RNA in large amounts at a reasonable price.

Typically, RNA is produced by RNA in vitro transcription reactions using an appropriate DNA template. In order to obtain homogenous RNA suitable for RNA-based therapeutics, the RNA has to be of a distinct length, which is achieved by precise termination of the RNA in vitro transcription reaction. A common way of controlling RNA in vitro transcription termination is the linearization of the DNA template right after the RNA coding sequence. This way, a so called run-off RNA in vitro transcription is achieved.

For obtaining high-grade RNA suitable to be used in therapy, various quality control steps have to be performed such as ensuring proper linearization of the DNA template and also removal of the DNA template from the RNA product later on by DNA digestion and subsequent RNA purification.

Hence, one critical step in RNA production is the generation of a suitable DNA template, which at industrial scale is a major cost factor. However, currently, DNA templates can often only be used for a single RNA in vitro transcription reaction and need subsequently be destroyed by DNAse digestion and removed by RNA purification in order to ensure efficacy and safety of the RNA-based therapeutics. Residual amounts of DNA in the final RNA-based therapeutic may induce activation of the innate immune system and have the potential to act as an oncogene in a patient.

Thus, there is a need to provide a reusable DNA template which can easily and effectively be separated from the RNA in vitro transcription reaction without its destruction.

Marble and Davis describe the RNA in vitro transcription from DNA templates which are associated with agarose beads and can therefore be re-used by recovery of the beads using mild centrifugation. In particular, the DNA template to be used in an RNA in vitro transcription reaction is associated with streptavidin-coated agarose beads via a single biotin at the 5' end of the non-template strand of the DNA template (Marble and Davis, Biotechnol. Prog. 1995, 11, 393-396). Furthermore, Liu and Price describe RNA in vitro transcription from DNA templates which are associated to streptavidin coated paramagnetic particles via 5' bound biotin, which has been added to the DNA template via polymerase chain reaction (PCR) using a biotinylated primer (Liu and Price, Promega Notes, 64, 1997, 21-26). Fujita and Silver describe RNA in vitro transcription from linear double stranded DNA templates with a T7 or T3 RNA polymerase promoter at one end and a single biotin moiety at the other end attached to streptavidin-coated paramagnetic beads (Fujita and Silver, Biotechniques Rapid Dispatches, 14(4) 1993, 608-617). Fujita and Silver conclude that, when the DNA was oriented so that the transcription proceeded toward the bead and the DNA was attached by a biotin-dUTP or biotin-dATP moiety at the 3' end of the non-template strand, the yield and quality of RNA synthesized was grossly equivalent to that made in solution.

PCR-based association of DNA templates (e.g. to agarose or to magnetic particles) as described above have the disadvantage that the association is sequence dependent (e.g. different primer pairs have to be designed for each individual DNA construct) and that PCR-based production of the DNA template is error-prone. Furthermore, the afore-described laboratory methods are not suitable for RNA production in large quantities on an industrial scale.

Although chemical, non-PCR-based DNA immobilization techniques are known, these do not provide for a directed coupling of DNA to a single support or tag. However, when coupling a DNA template to a support or tag for easy and effective separation of said template from an RNA in vitro transcription reaction, it is important that this coupling is done in a directed fashion e.g. not to impair efficient run-off of the RNA polymerase (RNAP) which ensures RNA products of homogenous length (see FIG. 1).

Thus, no methods are currently available which allow for a directed non-sequence, non-PCR-based coupling of a support or a tag to a linear DNA template after it is generated (e.g. after DNA preparation from an organism).

Accordingly, there is the need for providing high-quality linear DNA templates, which are associated with a support or a tag at the desired end of the linear DNA template and which can be produced at relatively low cost in large amounts so that RNA in vitro transcription on an industrial scale will become feasible.

SUMMARY OF THE INVENTION

The present invention solves the above needs, inter alia by providing linear double stranded DNA as described below in a first aspect of the invention and by providing methods of producing said linear double stranded DNA as described in aspects 2A-2D. In a third and fourth aspect, the present invention relates to the use of the DNA of aspect 1 of the present invention for RNA in vitro transcription and to a method for producing RNA in vitro comprising the use of the DNA of aspect 1. The present invention furthermore relates to a bioreactor for RNA in vitro transcription and a kit comprising parts which enables a person to produce the linear double stranded DNA of aspect 1 of the invention according to the methods of aspects 2A-2D of the invention.

All embodiments mentioned in the following chapters relate to the specific aspect of this chapter.

First Aspect: Linear Double Stranded DNA Coupled to a Single Support or Tag at the 3' End of its Non-Codinq Strand In a first aspect, the present invention relates to a linear double stranded DNA comprising a coding strand and a non-coding strand, wherein said DNA comprises a coding sequence element encoded by the coding strand, wherein said non-coding strand is coupled at its 3' end to a support or a tag, and wherein said support or tag is the only support or tag coupled to said DNA.

In a particularly preferred embodiment, the present invention relates to a linear double stranded DNA comprising a coding strand and a non-coding strand, wherein said DNA comprises a coding sequence element encoded by the coding strand, wherein said non-coding strand is coupled at its 3' end to a tag, and wherein the tag is the only tag coupled to said DNA.

In a specific embodiment, the non-coding strand coupled at its 3' end to a support or tag has at least one, preferably exactly one, deoxynucleotide overhang compared to 5' end of the complementary coding strand. Suitably, the at least one deoxynucleotide overhang is at least one deoxyadenosine, in particular exactly one deoxyadenosine.

The linear double stranded DNA may be a linearized DNA plasmid, e.g. a linearized bacterial DNA plasmid, a linearized Doggybone™ DNA (dbDNA), linear synthetic DNA, a PCR-amplified DNA, linearized viral DNA, or linear eukaryotic DNA, e.g. linear human DNA.

In a specific embodiment, the present invention relates to a linear double stranded DNA, which is coupled at the 3' end of its non-coding strand to a support or a tag via a triazole. The triazole may be an 1,2,3-triazole. In a preferred embodiment, the triazole is formed during a reaction, in particular of a cycloaddition (Azide-Alkyne Huisgen Cycloaddition) of an azide-activated support or tag with an alkyne deoxynucleotide of the DNA.

In another specific embodiment, the present invention relates to a linear double stranded DNA, which is coupled at the 3' end of its non-coding strand to a support or a tag via a dihydropyrazine moiety.

In another specific embodiment, the support is selected from the group consisting of a magnetic bead or particle, a nanobead or nanoparticle, agarose, an agarose bead or particle, glass, a glass bead or particle, poly(methyl methacrylate), a microchip, sepharose, sephadex and silica. In a preferred embodiment, the support is a magnetic bead or particle.

In a further specific embodiment, the tag is selected from the group consisting of biotin, PEG and FLAG. In a preferred embodiment, the tag is biotin. In an especially preferred embodiment, said biotin is associated with streptavidin, preferably with a streptavidin coated bead, most preferably with a streptavidin coated magnetic bead.

In another specific embodiment, the coding sequence element of the linear double stranded DNA is flanked by a 5' UTR and/or a 3' UTR. In a preferred embodiment, the 3' UTR is derived from an albumin gene, preferably a human albumin gene, or human alpha- or beta-globin gene. Further suitable 3'-UTRs are described in WO2016/107877 and WO2017/036580, particularly 3'-UTR elements according to SEQ ID NOs: 1 to 24 and SEQ ID NOs: 49 to 318 of the patent application WO2016/107877 or SEQ ID NOs: 152 to 204 of the patent application WO2017/036580. In another preferred embodiment, the 5' UTR is derived from the 32L4 ribosomal protein 32L4 TOP. In an especially preferred embodiment, the 3' UTR is derived from albumin and the 5' UTR is derived from the 32L4 ribosomal protein 32L4 TOP. Further suitable 5'-UTRs are described in WO2016/107877 and WO2017/036580, particularly 3'-UTR elements according to SEQ ID NOs: 25 to 30 and SEQ ID NOs: 319 to 382 of the patent application WO2016/107877 or SEQ ID NOs: 1 to 151 of the patent application WO2017/036580.

The linear double stranded DNA may further comprise a histone-stem-loop structure involved in nucleocytoplasmic transport of RNAs. A histone stem-loop sequence may be preferably derived from formulae (I) or (II) of the patent application WO2012/019780. According to a further preferred embodiment the RNA as defined herein may comprise at least one histone stem-loop sequence derived from at least one of the specific formulae (Ia) or (IIa) of the patent application WO2012/019780. Further, the linear double stranded DNA may comprise a stretch of at least 50 adenosines encoding a poly-A-tail as part of the 3' UTR and/or a stretch of at least 20 cytosines encoding a poly-C-tail as part of the 3' UTR and/or a spacer sequence at the 3' end of a promotor sequence element in order to separate it from a support or tag. Moreover, the linear double stranded DNA may be optimized regarding its GC content in order to make it more stable.

In a further specific embodiment, the double stranded DNA comprises 5' of the coding sequence element an RNA polymerase promotor sequence element. In a preferred embodiment, the RNA polymerase promotor sequence element is selected from a T3, T7, Sny5 or SP6 RNA polymerase promotor sequence.

In a second aspect, the present invention relates to methods (2A to 2E) of producing the linear double stranded DNA of the first aspect.

Second Aspect: Methods of Producing the Above DNA
Aspect 2A of the Second Aspect: Digestion of the DNA (c) Followed by Coupling (d)

In aspect 2A, the present invention relates to a method for producing linear double stranded DNA as described in aspect 1 of the present invention, the method comprising the steps of: (a) providing linear double stranded DNA comprising a sequence element encoded by the coding strand, which is followed at the 3' end by a restriction site element, (b) adding a modified deoxynucleotide to the 3' end of each strand of the provided DNA, (c) cutting the DNA at the restriction site in order to remove the modified deoxynucleotide from the 3' end of the coding strand and (d) coupling the remaining modified deoxynucleotide at the 3' end of the non-coding strand to a support or a tag.

Hence, in aspect 2A the present invention relates to a method for producing linear double stranded DNA comprising a coding strand and a non-coding strand, wherein said non-coding strand is coupled at its 3' end to a support or a tag, comprising the steps of:
(a) providing linear double stranded DNA comprising a coding sequence element encoded by the coding strand, followed at the 3' end by a restriction site element;
(b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
(c) incubating the DNA obtained in step (b) with a restriction endonuclease recognizing said restriction site element in order to obtain linear double stranded DNA with a modified deoxynucleotide at the 3' end of the non-coding strand;
(d) coupling the DNA obtained in step (c) via its modified deoxynucleotide to a support or a tag in order to provide linear double stranded DNA, wherein the non-coding strand of said DNA is coupled at its 3' end to a support or a tag.

An exemplary illustration of the above-described method can be found in FIG. 2.

Aspect 2B of the Second Aspect: Coupling to the DNA (c) Followed by Digestion (d)

In aspect 2B, the present invention relates to a method for producing linear double stranded DNA as described in aspect 1 of the present invention, the method comprising the steps of: (a) providing linear double stranded DNA comprising a sequence element encoded by the coding strand, which is followed at the 3' end by a restriction site element, (b) adding a modified deoxynucleotide to the 3' end of each strand of the provided DNA but (c) contrary to the method described in aspect 2A said modified deoxynucleotides are directly coupled to a support or at tag and (d) only then is the DNA, which is coupled to a support or tag on both of its 3' ends, cut at the restriction site in order to remove the support or tag from the 3' end of the coding strand.

Hence, in aspect 2B the present invention relates to a method for producing linear double stranded DNA comprising a coding strand and a non-coding strand, wherein said non-coding strand is coupled at its 3' end to a support or a tag, comprising the steps of:
(a) providing linear double stranded DNA comprising a coding sequence element encoded by the coding strand, followed at the 3' end by a restriction site element;
(b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
(c) coupling the DNA obtained in step (b) via the modified deoxynucleotide at the 3' end of each strand to a support or a tag;
(d) incubating the DNA obtained in step (c) with a restriction endonuclease recognizing said restriction site element in order to provide linear double stranded DNA, wherein the non-coding strand of said DNA is coupled at its 3' end to a support or a tag.

The following embodiments relate to methods as described in aspects 2A and 2B.

In a specific embodiment, the modified deoxynucleotide is selected from the group consisting of an alkyne deoxynucleotide, an azide deoxynucleotide, an azadibenzo-cyclooctyne deoxynucleotide, a trans-cyclooctene deoxynucleotide, and a vinyl deoxynucleotide.

In another specific embodiment, the enzyme capable of adding a modified deoxynucleotide at the 3' end of a strand in step (b) is a DNA polymerase. In a preferred embodiment, the DNA polymerase is selected from the group of a *Thermus aquaticus* DNA polymerase, an *Escherichia coli* DNA polymerase, a *Saccharomyces cerevisiae* DP1 DNA polymerase, a mammalian DNA 13 polymerase, an engineered DNA polymerase, a DNA polymerase I large (Klenow) fragment and a terminal transferase. In an especially preferred embodiment, the DNA polymerase is a *Thermus aquaticus* DNA polymerase. Since *Thermus aquaticus* DNA polymerase adds adenine nucleotides exclusively to the blunted 3' ends of double stranded linear DNA, it is understood that if a *Thermus aquaticus* DNA polymerase is used, the linearized DNA provided in step (a) must comprise at least one blunted end at the 5' end of the coding sequence element.

Generally, it is desired that when adding a modified nucleotide to the 3' end of a DNA strand, the DNA polymerase has no 3'-5' exonuclease activity. Engineered DNA polymerases may therefore be genetically engineered to eliminate the 3' to 5' proofreading exonuclease activity associated with many DNA polymerases. Examples of engineered DNA polymerases are Vent (exo-) DNA polymerase and Deep Vent (exo-) DNA polymerase of New England BioLabs (NEB) as well as Platinum® Th Exo(-) DNA polymerase of invitrogen.

In a specific embodiment, the support is selected from the group consisting of a magnetic bead or particle, a nanobead or nanoparticle, agarose, an agarose bead or particle, glass, a glass bead or particle, poly(methyl methacrylate), a microchip, sepharose, sephadex and silica. In a preferred embodiment, the support is a magnetic bead or particle.

In a further specific embodiment, the tag is selected from the group consisting of biotin, PEG and FLAG. In a preferred embodiment, the tag is biotin.

In another specific embodiment, the support or the tag used in the coupling step of the afore-described methods is an activated support or an activated tag.

In one embodiment, the activated support or tag is selected from the group consisting of an alkyne-activated support or tag, an azide-activated support or tag, an azadibenzocyclooctyne-activated support or tag, a tetrazine-activated support or tag, and a trans-cyclooctene-activated support or tag.

"Click Chemistry" describes the rapid and highly selective reaction ("click") between pairs of chemically reactive groups and is widely used in areas such a bioscience, drug discovery, material science, and radiochemistry. Click chemistry reactions are highly selective and bio-orthogonal (that means neither the reactants' nor the products' reactive groups interact with the functional groups of the biomolecules such as DNA). They take place under physiological conditions (neutral pH, aqueous solution and ambient temperatures), result in little or no by-products therefore not requiring elaborate workup or purification of the product and hence produce high yields.

In a specific embodiment, the modified deoxynucleotide is coupled to the activated support or tag via metal-catalyzed azide-alkyne click chemistry (MARC), Cu(I)-catalyzed azide-alkyne click chemistry reaction (CuAAC), strain-promoted azide-alkyne click chemistry reaction (SPAAC) or tetrazine-alkene ligation. Suitable metals for catalyzation of click reactions are for example Cu, Ru, Ag, Au, Ir, Ni, Zn and Ln.

In a preferred embodiment, the modified deoxynucleotide is coupled to the activated support or tag via CuAAC, SPAAC or tetrazine-alkene ligation.

The most prominent example of click chemistry is the CuAAC reaction, where a terminal alkyne-activated molecule reacts with an azide-activated molecule forming a triazole moiety in the presence of Cu(I) ions. Different copper sources are available such as $CuSO_4$, CuBr or CuOAc. Preferably, water-soluble $CuSO_4$ is used.

In a specific embodiment, the modified deoxynucleotide is an alkyne deoxynucleotide and the activated support or tag is an azide-activated support or tag. In one embodiment, the modified deoxynucleotide is selected from an ethynyl-dNTP such as for example a 2-ethynyl-dNTP and a 5-ethynyl-dNTP and a propargyl-dNTP such as for example a $N^6$-propargyl-dNTP, a γ-[(propargyl)-imido]-dNTP and a 3'-(O-propargyl)-dNTP. The base is selected from adenine, guanine, cytosine and thymine.

In a preferred embodiment, the modified deoxynucleotide is an ethynyl deoxynucleotide, preferably an ethynyl-deoxyadenosine triphosphate (ethynyl-dATP).

In a specific embodiment, the modified deoxynucleotide is an azide deoxynucleotide and the activated support or tag is an alkyne-activated support or tag. In a preferred embodiment, the azide deoxynucleotide is selected from the group consisting of 8-azido-d NTP, γ-(2-azidoethyl)-dNTP, γ-(6-azidoethyl)-d NTP, γ-[(6-azidohexyl)-imido]-dNTP, N6-(6-azido)hexyl-d NTP, N6-(6-azido)hexyl-3'-d NTP, 3'-azido-2',3'dNTP (azNTP), 5-azidomethyl-d NTP, azide-PEG4-aminoallyl-dNTP, 5-azido-C3 dNTP, 5-azido-PEG4-d NTP and 3'-O-azidomethyl-d NTP. The base is selected from adenine, guanine, cytosine and thymine.

A potential issue with CuAAC reaction on DNA is that Cu(I) ions may yield DNA strand breaks and therefore damage DNA. However, this issue can be overcome by using Cu(I)-chelating ligands such as tris[(1-benzyl-1H-1,2,3-triazol-4-yl)methyl]amine (TBTA), 3-[4-[[bis[[1-(3-hydroxypropyl)triazol-4-yl]methyl]amino]methyl]triazol-1-yl]propan-1-ol (THPTA), 2-(4-((bis((1-(tert-butyl)-1H-1,2,3-triazol-4-yl)methyl)amino)methyl)-1H-1,2,3-triazol-1-yl) acetic acid (BTTAA) and its tert-butyl analog TTTA. Those ligands do not only protect the DNA from oxidative damage but also accelerate the CuAAC reaction by stabilizing copper ions in the Cu(I) oxidation state.

In a specific embodiment, the coupling step is performed in the presence of Cu(I)-TBTA, Cu(I)-THPTA (water-soluble alternative to TBTA), Cu(I)-BTTAA or Cu(I)-TTTA. In a preferred embodiment, the coupling step is performed in the presence of Cu(I)-TBTA or Cu(I)-THPTA. In a most preferred embodiment, the coupling step is performed in the presence of Cu(I)-THPTA.

Using ethylenediaminetetraacetic acid (EDTA) is a way of complexing and removing Cu(I) ions after the coupling step.

In a specific embodiment, an additional washing step is performed in order to remove Cu(I) via complexation to EDTA after the coupling step.

A copper free alternative to CuAAC is SPAAC, a reaction that relies on the use of strained cyclooctynes with little activation energy compared to terminal alkynes. Strained cyclooctynes react with azid-activated molecules without the need for exogenous catalysts.

In a specific embodiment, the modified deoxynucleotide is an azadibenzo-cyclooctyne deoxynucleotide and the activated support or tag is an azide-activated support or tag. In a preferred embodiment, the azadibenzocyclooctyne deoxynucleotide is 5-DBCO-$PEG_4$-dNTP. The base is selected from adenine, guanine, cytosine and thymine. In a most preferred embodiment, the azadibenzo-cyclooctyne deoxynucleotide is 5-DBCO-$PEG_4$-dATP.

In another specific embodiment, the modified deoxynucleotide is an azide deoxynucleotide and the activated support or tag is an azadibenzo-cyclooctyne-activated support or tag. In a preferred embodiment, the azide deoxynucleotide is selected from the group consisting of 8-azido-dNTP, γ-(2-azidoethyl)-dNTP, γ-(6-azidoethyl)-dNTP, γ-[(6-azidohexyl)-imido]-dNTP, N6-(6-azido)hexyl-d NTP, N6-(6-azido)hexyl-3'-dNTP, 3'-azido-2',3'd NTP (azNTP), 5-azidomethyl-d NTP, azide-PEG4-aminoallyl-dNTP, 5-azido-C3 dNTP, 5-azido-PEG4-dNTP and 3'-O-azidomethyl-dNTP. The base is selected from adenine, guanine, cytosine and thymine.

Another non-toxic very efficient reaction is the tetrazine-alkene ligation, where a tetrazine-activated molecule reacts with a terminal or strained alkene-activated molecule. Both molecules are then connected via a dihydropyrazine.

In a specific embodiment, the modified deoxynucleotide is a trans-cyclooctene and the activated support or tag is a tetrazine-activated support or tag. In a preferred embodiment, the trans-cyclooctene deoxynucleotide is 5-TCO-$PEG_4$-dNTP. The base is selected from adenine, guanine, cytosine and thymine. In an especially preferred embodiment, the trans-cyclooctene deoxynucleotide is 5-TCO-$PEG_4$-dATP.

In another specific embodiment, the modified deoxynucleotide is a vinyl deoxynucleotide and wherein the activated support or tag is a tetrazine-activated support or tag. In a preferred embodiment, the vinyl deoxynucleotide is 5-vinyl-dNTP. The base is selected from adenine, guanine, cytosine and thymine. In an especially preferred embodiment, the vinyl deoxynucleotide is 5-vinyl-dATP.

Digestion of linear double stranded DNA obtained in step (b) or (c) of the methods described above at its restriction site will result in two DNA fragments. In order to separate the linear double stranded DNA fragment with a modified deoxynucleotide or support or tag at the 3' end of the non-coding strand from linear double stranded DNA with a modified deoxynucleotide or support or tag at the 3' end of the coding strand an additional washing step may be performed after restriction. In a specific embodiment, the separation is achieved via the size of the DNA fragments. In a preferred embodiment the smaller fragment is removed using AMPure XP beads (Beckman Coulter).

In a specific embodiment, the restriction site element is selected from a XbaI, PvuII or EcoRI site. Preferably, the restriction site element is an EcoRI site and the restriction endonuclease used is EcoRI.

In another specific embodiment, the restriction site element is located at the position where run-off of the RNA polymerase during RNA in vitro transcription is desired. In other words, the restriction site element is located at the position where termination of the RNA in vitro transcription reaction is desired to generate an RNA product of a defined size.

Aspect 2C of the Second Aspect: Tagging of the DNA (b) Followed by Digestion (c)

Although "click" reactions take place under mild conditions with almost no by-products and are mostly non-toxic, it is sometimes desired to unilaterally tag DNA not by chemical but by enzymatic means.

In aspect 2C, the present invention relates to a method for producing linear double stranded DNA as described in aspect 1 of the present invention, in particular to the production of a linear double stranded DNA, wherein the 3' end of the non-coding strand is coupled to a tag. The method of aspect 2C comprises the steps of: (a) providing linear double stranded DNA comprising a coding sequence element encoded by the coding strand, followed at the 3' end by a restriction site element, (b) different from the afore-mentioned methods of aspects 2A and 2B, adding to the 3' end of each strand of said DNA a deoxynucleotide which is already linked to a tag and (c) cutting the DNA obtained in step (b) in order to remove the support or tag from the 3' end of the coding strand.

Hence, in aspect 2C, the present invention relates to a method for producing linear double stranded DNA comprising a coding strand and a non-coding strand, wherein said non-coding strand is coupled at its 3' end to a tag, comprising the steps of:
(a) providing linear double stranded DNA comprising a coding sequence element encoded by the coding strand, followed at the 3' end by a restriction site element;
(b) incubating said DNA with (i) a tag-linked deoxynucleotide and (ii) an enzyme capable of adding a tag-linked deoxynucleotide at a 3'end of a strand in order to provide linear double stranded DNA with a tag-linked deoxynucleotide at the 3' end of each strand;
(c) incubating the DNA obtained in step (b) with a restriction endonuclease recognizing said restriction site element in order to obtain linear double stranded DNA, wherein the non-coding strand of said DNA is coupled at its 3' end to a tag.

In a specific embodiment, the tag-linked deoxynucleotide is selected from the group consisting of a biotin-deoxynucleotide and a PEG-deoxynucleotide. In a preferred embodiment, the tag-linked deoxynucleotide is a biotin-dNTP or a PEG-dNTP. The base is selected from adenine, guanine, cytosine and thymine. In a more preferred embodiment, the tag-linked deoxynucleotide is a biotin-dNTP (biotinylated dNTP). In an even more preferred embodiment the biotin-dNTP (biotinylated dNTP) is a biotin-dATP (biotinylated dATP).

In another specific embodiment, the enzyme capable of adding a tag-linked deoxynucleotide at the 3' end of a strand in step (b) is selected from the group of a *Thermus aquaticus* DNA polymerase, an *Escherichia coli* DNA polymerase, a *Saccharomyces cerevisiae* DP1 DNA polymerase, a mammalian DNA 13 polymerase, an engineered DNA polymerase, a DNA polymerase I large (Klenow) fragment and a terminal transferase. In a preferred embodiment the enzyme capable of adding a tag-linked deoxynucleotide at the 3' end of a strand in step (b) is a *Thermus aquaticus* DNA polymerase or a terminal transferase. In an especially preferred embodiment the enzyme capable of adding a tag-linked deoxynucleotide at the 3' end of a strand in step (b) is a *Thermus aquaticus* DNA polymerase. Since *Thermus aquaticus* DNA polymerase adds adenine nucleotides exclusively to the blunted 3' ends of double stranded linear DNA, it is understood that if a *Thermus aquaticus* DNA polymerase is used, the linearized DNA provided in step (a) must comprise at least one blunted end at the 5' end of the coding sequence element.

As already mentioned digestion of linear double stranded DNA obtained in step (b) at its restriction site will result in two DNA fragments. In order to separate the linear double stranded DNA fragment with a tag-linked deoxynucleotide at the 3' end of the non-coding strand from linear double stranded DNA with a tag-linked deoxynucleotide at the 3' end of the coding strand an additional washing step may be performed after restriction. In a specific embodiment, the separation is achieved via the size of the DNA fragments. In a preferred embodiment the smaller fragment is removed using AMPure XP beads (Beckman Coulter).

In a specific embodiment, the restriction site element is selected from a XbaI, PvuII or EcoRI site. Preferably, the restriction site element is an EcoRI site and the restriction endonuclease used is EcoRI.

In another specific embodiment, the restriction site element is located at the position where run-off of the RNA polymerase during RNA in vitro transcription is desired.

Aspect 2D and 2E of the Second Aspect: Specific Coupling to/Tagging of the DNA

An even faster method of enzymatically coupling or tagging DNA is to specifically couple and/or tag the 3' end of the non-coding strand of a linear double stranded DNA by inter alia providing linear double stranded DNA comprising a sequence element encoded by the coding strand, wherein said DNA has a blunt end 5' of said coding element and a sticky end 3' of said coding element.

Hence, in aspect 2D, the present invention relates to a method for producing linear double stranded DNA comprising a coding strand and a non-coding strand, wherein said non-coding strand is coupled at its 3' end to a support or a tag, comprising the steps of:
(a) providing linear double stranded DNA comprising a coding sequence element encoded by the coding strand, wherein said DNA has a blunt end 5' of said coding element and a sticky end 3' of said coding element;
(b) incubating said DNA with (i) a modified deoxynucleotide and (ii) an enzyme capable of adding said modified deoxynucleotide at a blunt end to the 3' end of a single strand and not at a sticky end in order to provide linear double stranded DNA with a modified deoxynucleotide at the 3' end of the non-coding strand;
(c) coupling the DNA obtained in step (b) via its modified deoxynucleotide to a support or a tag in order to provide linear double stranded DNA, wherein the non-coding strand of said DNA is coupled at its 3' end to a support or a tag.

In aspect 2E, the present invention relates to a method for producing linear double stranded DNA comprising a coding strand and a non-coding strand, wherein said non-coding strand is coupled at its 3' end to a tag, comprising the steps of:
(a) providing linear double stranded DNA comprising a coding sequence element encoded by the coding strand, wherein said DNA has a blunt end 5' of said coding element and a sticky end 3' of said coding element;
(b) incubating said DNA with (i) a tag-linked deoxynucleotide and (ii) an enzyme capable of adding a tag-linked deoxynucleotide at a blunt end to the 3' end of a single strand and not at a sticky end in order to provide linear double stranded DNA with a tag-linked deoxynucleotide at the 3' end of the non-coding strand.

The following embodiments relate to methods as described in aspects 2D and 2E.

In a specific embodiment, the enzyme capable of adding a modified deoxynucleotide or tag-linked deoxynucleotide exclusively to a blunt end but not to a sticky end is a *Thermus aquaticus* DNA polymerase or the Platinum® Th Exo(-) DNA polymerase of Invitrogen.

In another specific embodiment, the sticky end 3' of the coding sequence element of the DNA is at the position where run-off of the RNA polymerase during RNA in vitro transcription is desired.

Third Aspect: Use of the Linear Double Stranded DNA of Aspect 1 of the Present Invention In a third aspect, the present invention relates to the use of linear double stranded DNA comprising a coding strand and a non-coding strand, wherein said DNA comprises a coding sequence element encoded by the coding strand, wherein said non-coding strand is coupled at its 3' end to a support or a tag, and wherein said support or tag is the only support or tag coupled to said DNA in an RNA in vitro transcription reaction.

In a specific embodiment, the present invention relates to the use of linear double stranded DNA, which is coupled at the 3' end of its non-coding strand to a support or a tag via a triazole, in an RNA in vitro transcription reaction.

In another specific embodiment, the present invention relates to the use of a linear double stranded DNA, which is coupled at the 3' end of its non-coding strand to a support or a tag via a dihydropyrazine moiety, in an RNA in vitro transcription reaction.

In a further specific embodiment, the support coupled to the 3' end of the non-coding strand of the linear double stranded DNA to be used in an RNA in vitro transcription reaction is selected from the group consisting of a magnetic bead or particle, a nanobead or nanoparticle, agarose, an agarose bead or particle, glass, a glass bead or particle, poly(methyl methacrylate), a microchip, sepharose, sephadex and silica. In a preferred embodiment, the support coupled to the 3' end of the non-coding strand of the linear double stranded DNA to be used in an RNA in vitro transcription reaction is a magnetic bead or particle.

In another specific embodiment, the tag coupled to the 3' end of the non-coding strand of the linear double stranded DNA to be used in an RNA in vitro transcription reaction is selected from the group consisting of biotin, PEG and FLAG. In a preferred embodiment, the tag is biotin. In an especially preferred embodiment, said biotin is associated with streptavidin, preferably with a streptavidin coated bead, most preferably with a streptavidin coated magnetic bead. This is exemplary shown in FIG. 4.

In another specific embodiment, the coding sequence element of the linear double stranded DNA to be used in an RNA in vitro transcription reaction is flanked by a 5' UTR and/or a 3' UTR. In a preferred embodiment, the 3' UTR is derived from albumin. In another preferred embodiment, the 5' UTR is derived from the 32L4 ribosomal protein 32L4 TOP. Further suitable UTRs in that context are specified in aspect 1 of the invention.

In an especially preferred embodiment, the 3' UTR is derived from albumin and the 5' UTR is derived from the 32L4 ribosomal protein 32L4 TOP.

In a further specific embodiment, the double stranded DNA to be used in an RNA in vitro transcription comprises 5' of the coding sequence element an RNA polymerase promotor sequence element. In a preferred embodiment, the RNA polymerase promotor sequence element is selected from a T3, T7, Sny5 or SP6 RNA polymerase promotor sequence.

Fourth Aspect: Method for Producing RNA In Vitro Using the Double Stranded Linear DNA of Aspect 1 of the Invention as a Template In a fourth aspect, the present invention relates to a method for producing RNA in vitro comprising the steps of:

(a) providing the double stranded linear DNA as described herein as template DNA;
(b) providing (i) nucleoside triphosphates and (ii) a DNA-dependent RNA polymerase;
(c) incubating the DNA provided in step (a) with (i) and (ii) provided in step (b) under suitable conditions in order to produce RNA.

In a preferred embodiment of the fourth aspect, the double stranded linear DNA referred to under (a) above is coupled at its 3' end to a support as specified herein (either via a direct coupling to the support or via an association of the tag coupled to the DNA with the support) in order to immobilize the linear DNA. This allows for a separation of the DNA from the reaction mixture after RNA in vitro transcription took place (as further specified in the fifth aspect). Preferably, the support coupled the linear DNA (being the template DNA) as provided in step (a) is a magnetic bead.

Methods for producing RNA in vitro (i.e. in a cell-free environment) under suitable conditions are known in the art (see for example Geall et al. (2013) Semin. Immunol. 25(2): 152-159, Brunelle et al. (2013) Methods Enzymol. 530: 101-14). An example how to put such a method into practice can be found in Example 1, 4 and 5.

In a specific embodiment, the DNA-dependent RNA polymerase in step (b) is a bacteriophage RNA polymerase, preferably a T3, T7, Syn5 or SP6 DNA-dependent RNA polymerase.

In another specific embodiment, one of the following independently selected from a cap analogue, a ribonuclease inhibitor, a pyrophosphatase and a $MgCl_2$ is additionally provided in step (b).

Examples of cap analogs are m7GpppG, m7GpppA, m7GpppC; unmethylated cap analogs (e.g., GpppG); dimethylated cap analog (e.g., m2,7GpppG), trimethylated cap analog (e.g., m2,2,7GpppG), dimethylated symmetrical cap analogs (e.g., m7Gpppm7G), or anti reverse cap analogs (e.g., ARCA; m7,2'OmeGpppG, m7,2'dGpppG, m7,3'Ome-GpppG, m7,3'dGpppG and their tetraphosphate derivatives) (Stepinski et al., 2001. RNA 7(10):1486-95). Further cap analogs have been described previously (U.S. Pat. No. 7,074,596, WO 2008/016473, WO 2008/157688, WO 2009/149253, WO 2011/015347, and WO 2013/059475). The synthesis of N7-(4-chlorophenoxyethyl) substituted dinucleotide cap analogs has been described recently (Kore et al., 2013. Bioorg. Med. Chem. 21(15):4570-4).

In a preferred embodiment, the cap analogue is m7G(5') ppp(5')G(m7G).

In a specific embodiment, the DNA is incubated in step (c) in a buffer suitable for producing RNA in vitro.

Common buffers used for the production of RNA in vitro include Tris (2-amino-2-hydroxymethyl-propane-1,3-diol) and HEPES (2-[4-(2-hydroxyethyl)piperazin-1-yl]ethanesulfonic acid). The buffer substance may further comprise an acid or a base for adjusting the pH, such as or citric acid or HCl in case of Tris and KOH in case of HEPES. The pH value of the buffer is commonly adjusted to a pH value of 6 to 8.5. Some commonly used transcription buffers comprise HEPES/KOH, pH 7.5 and Tris/HCL, pH 7.5.

In another specific embodiment, the template DNA provided in step (a) is re-used in at least one further RNA in vitro production cycle. This is exemplary shown in FIG. 3.

In vitro RNA production may be stopped by addition of EDTA.

Fifth Aspect: Bioreactor

In a fifth aspect, the present invention relates to a bioreactor for RNA in vitro transcription comprising (a) a reaction vessel (13) comprising the linear double stranded DNA as described herein;
(b) a vessel (14) comprising ribonucleoside triphosphates and DNA-dependent RNA polymerase, wherein said vessel is connected to the reaction vessel; and
(c) a product vessel (15) for collecting the RNA product, wherein said vessel is also connected to the reaction vessel.

The bioreactor may be thermally regulated to maintain accurately a specific temperature, usually between 4 and 40° C.

The vessel (14) may additionally comprise at least one of the following independently selected from a cap analogue, a ribonuclease inhibitor, a pyrophosphatase, a $MgCl_2$, a buffer suitable for RNA in vitro transcription, an antioxidant and a polyamine.

Examples for cap analogues and buffers are the same as listed above under aspect 3 of the present invention.

Examples for antioxidants are DTT (dithiothreitol), TCEP (tris(2-carboxyethyl)phosphine), NAC (N-acetylcysteine), beta-mercaptoethanol, glutathione, cysteine and cystine.

Examples for polyamines are spermine and spermidine.

The components present in vessel (14) can be released into the reaction vessel (13) in a certain amount at a certain time. Once, the components of vessel (14) have been released into reaction vessel (13), RNA in vitro transcription starts. After termination of RNA in vitro transcription e.g. by addition of EDTA into reaction vessel (13), the RNA can be released into a product vessel (15) for collecting the RNA product.

In a specific embodiment, the reaction vessel (13) comprises linear double stranded DNA comprising a coding strand and a non-coding strand, wherein said DNA comprises a coding sequence element encoded by the coding strand, wherein said non-coding strand is coupled at its 3' end to biotin, which in turn is associated to a streptavidin coated magnetic bead.

In another specific embodiment, a magnet is surrounding the reaction vessel (13) from the outside. In a preferred embodiment the magnet is an electro magnet.

In a further specific embodiment, the magnet is capable of oscillating between two states in order to create an oscillating magnetic field which is capable of inducing flows within the mixture in reaction vessel (13), thereby leading to the mixing of said reaction mixture.

In another specific embodiment, the magnet is capable of attracting the linear double stranded DNA coupled at the 3' end of its non-coding strand to biotin, which in turn is associated to a streptavidin coated magnetic bead. Attraction via the magnet can be tightly controlled in order to separate the DNA template from the RNA product. In a further embodiment, the RNA product is collected in the product vessel (15).

In another specific embodiment, the support or tag of the linear DNA comprised by the reaction vessel (13) is linked to said reaction vessel. The support or tag may be linked to the reaction vessel (13) either covalently or non-covalently. In one embodiment, the support or tag is covalently linked to the reaction vessel (13) in order to immobilize the linear DNA permanently within the reaction vessel (13).

In a further specific embodiment, the reaction vessel (13) comprises at least one means for measuring and/or adjusting pH, salt concentration, magnesium concentration, phosphate concentration, temperature, pressure, flow velocity, RNA concentration and/or ribonucleotide triphosphate concentration.

In another specific embodiment, the bioreactor comprises a filtration membrane between the reaction vessel (13) and the product vessel (15), preferably an ultrafiltration membrane for separating the RNA product from the reaction mix. In a preferred embodiment, the filtration or ultrafiltration membrane has a cut-off in a range from 10 to 100 kDa, 10 to 75 kDa, 10 to 50 kDa, 10 to 25 kDa or 10 to 15 kDa. In another preferred embodiment, the filtration or ultrafiltration membrane is selected from the group consisting of regenerated cellulose, modified cellulose, polysulfone, polyethersulfone, polyacrylonitrile, polymethylmethacrylate, polyvinyl alcohol and polyarylethersulfone.

In a further specific embodiment, the product vessel (15) comprises a resin to capture the produced RNA in order to separate the RNA product from other soluble low molecular weight components.

The bioreactor may be operated in a batch mode so that all reagents are present at the beginning of the RNA in vitro transcription reaction and no new reactions are added and no product is removed until the transcription reaction has or is stopped. Alternatively, the bioreactor may be operated in a semi-batch mode, which refers to a repetitive series of transcription reactions, where the product is removed after every transcription cycle and new reactants are added for the next transcription reaction. The bioreactor may also be operated in a continuous mode, where reactants are constantly supplied and products are constantly removed.

An example of a bioreactor for RNA in vitro transcription can be found in FIG. 4.

Bioreactors are commonly used for in vitro synthesis of RNA and known to the skilled person (see e.g. WO 95/08626).

Sixth Aspect: Kit

In a sixth aspect, the present invention relates to kits which provide essential components and enables a person to exert the methods as described in aspect 2 of the present invention. The initial DNA to be modified according to the present invention has to be provided by the person using the kit.

In aspect 6A, the present invention relates to a kit comprising:
(a) a modified deoxynucleotide;
(b) a *Thermus aquaticus* DNA polymerase capable of adding said modified deoxynucleotide to the 3' end of a strand at a blunt DNA end;
(c) an activated support or tag;
(d) a counterpart of said support or tag associating in a highly specific manner with said support or tag.

In aspect 6B, the present invention relates to a kit comprising:
(a) a tag-linked deoxynucleotide;
(b) a *Thermus aquaticus* DNA polymerase capable of adding said tag-linked deoxynucleotide to the 3' end of a strand at a blunt DNA end;
(c) a counterpart of said tag associating in a highly specific manner with said tag.

The following embodiment relates to kits as described in aspects 6A and 6B.

In a specific embodiment, the tag is biotin and the counterpart is avidin or streptavidin.

In a preferred embodiment, the present invention relates to a kit comprising:
(a) a modified deoxynucleotide;
(b) a *Thermus aquaticus* DNA polymerase capable of adding said modified deoxynucleotide to the 3' end of a strand at a blunt DNA end;
(c) activated-biotin;

(d) streptavidin-coupled magnetic beads;
(e) optionally, buffer for click chemistry.

In a more preferred embodiment, the modified deoxynucleotide is a modified dATP. In particular, the modified dATP is selected from alkyne dATP, an azide dATP, an azadibenzocyclooctyne dATP, a trans-cyclooctene dATP, and a vinyl dATP.

In another preferred embodiment, the present invention relates to a kit comprising:
(a) a biotin-linked deoxynucleotide;
(b) a *Thermus aquaticus* DNA polymerase capable of adding said tag-linked deoxynucleotide to the 3' end of a strand at a blunt DNA end;
(c) streptavidin-coupled magnetic beads.

In a more preferred embodiment, the biotin-linked deoxynucleotide is a biotin-linked dATP.

BRIEF DESCRIPTION OF THE DRAWINGS

The figures shown in the following are merely illustrative and shall describe the present invention in a further way. These figures shall not be construed to limit the present invention thereto.

FIG. 1A illustrates that non-directed coupling of supports (1) impedes run-off of the RNAP from a DNA template (2), which leads to abortive short RNA sequences (3) and a heterogeneous RNA product.

FIG. 1B illustrates that directed coupling of a support (1) leaving the RNA in vitro transcription termination position free (4) will allow for run-off of the RNAP and will result homogenous full length RNA transcripts (3).

FIG. 2 illustrates an example of the method as described in aspect 2A of the present invention. A circular plasmid DNA (5) is linearized using a blunt end restriction enzyme (6). Then a modified adenine deoxynucleotide (A*) is added to the 3' end of each strand of the linearized DNA using a DNA polymerase (7). In the next step, the DNA obtained in the previous step is restricted at a pre-determined restriction site (8). Finally, the restricted DNA is coupled to a support or tag (1) via the modified adenine deoxynucleotide (A*) in a last step (9), while leaving a free end for RNA in vitro transcription termination (4).

FIG. 3A illustrates linear double stranded DNA associated with a magnetic bead (1) via the 3' end of its non-coding strand, which serves as a template for run-off RNA in vitro transcription. Run-off RNA in vitro transcription results in RNA transcripts (3).

FIG. 3B illustrates that following RNA synthesis, linear double stranded template DNA associated with a magnetic bead can be captured by an electro magnet (10) and the RNA product can be separated from the captured DNA (11). The captured DNA can be re-used for further run-off RNA in vitro transcription cycles (12).

FIG. 4 shows a bioreactor for RNA in vitro transcription comprising a reaction vessel (13), which is surrounded by a magnet (10) and comprises linear double stranded DNA according to the invention, a vessel (14) comprising ribonucleoside triphosphates and DNA-dependent RNA polymerase connected to the reaction vessel (13) and a product vessel (15), which is connected to the reaction vessel for collection of the RNA product.

FIG. 5 shows the amount of soluble DNA (ng/µl) at different time points during the coupling reaction (30, 60, 120 and 240 minutes). A=XbaI-digested plasmid DNA coupled to 6 MB Sepharose; B=XbaI-digested plasmid DNA coupled to 4B Sepharose; C=PvuII-digested plasmid DNA coupled to 6 MB Sepharose; D=PvuII-digested plasmid DNA coupled to 4B Sepharose, see also Example 1.

FIG. 6B shows the amount of RNA (mg/µl) produced in an RNA in vitro assay using XbaI-linearized 6 MB sepharose-coupled DNA template (1, 2); XbaI-linearized 4B sepharose-coupled DNA template; (3, 4); PvuII-linearized 6 MB sepharose-coupled DNA template (5, 6); PvuII-linearized 4B sepharose-coupled DNA template (7, 8) and a free template DNA (positive control) (9).

FIG. 7 shows a digest of non-associated or streptavidin-associated DNA. To test association efficiency, non-associated DNA in supernatants (SN) was digested using NsbI resulting in two fragments of 1289 bp and 2586 bp. To test accessibility of enzymes, streptavidin-associated DNA was digested using NsbI resulting in one soluble DNA fragment of 2586 bp. 1: Marker; 2: SN before association with streptavidin, 3: SN after association with streptavidin; 4: SN after digestion of streptavidin associated DNA from beads. A detailed description of the experiment is provided in Example 3.

FIG. 8 shows RNA in vitro transcription from a streptavidin-associated DNA template. Either TBTA (A)- or THPTA (B)-catalyzed cycloaddition was performed and the biotin-coupled DNA template was either washed with 70% EtOH (wash I) or 70% EtOH/10 mM EDTA and 70% EtOH (wash II) before association with streptavidin coated magnetic beads prior to RNA in vitro transcription. 1: Marker; 2: dATP-adenylation, TBTA-catalyzed cycloaddition, wash I, association; 3: ethynyl-dATP-adenylation, TBTA-catalyzed cycloaddition, wash I, w/o association; 4: ethynyl-dATP-adenylation, TBTA-catalyzed cycloaddition, wash I, association; 5: ethynyl-dATP-adenylation, TBTA-catalyzed cycloaddition, wash II, association; 6: dATP-adenylation, THPTA-catalyzed cycloaddition, wash I, association; 7: ethynyl-dATP-adenylation, THPTA-catalyzed cycloaddition, wash I, w/o association; 8: ethynyl-dATP-adenylation, THPTA-catalyzed cycloaddition, wash I, association; 9: ethynyl-dATP-adenylation, THPTA-catalyzed cycloaddition, wash II, association; 10: ethynyl-dATP-adenylation, without cycloaddition. A detailed description of the experiment is provided in Example 4.

FIG. 9 shows RNA in vitro transcription from a streptavidin-associated DNA template. Either TBTA- or THPTA-catalyzed cycloaddition was performed and the biotin-coupled DNA template was either washed with 70% EtOH (wash I) or 70% EtOH/10 mM EDTA and 70% EtOH (wash II) before association with streptavidin coated magnetic beads prior to RNA in vitro transcription. To improve DNA quality after coupling and therefore RNA in vitro transcription conditions the biotin-coupled DNA was further washed six times with a wash buffer and three times with 1×TE (wash III). 1: Marker; 2: dATP-adenylating, TBTA-catalyzed cycloaddition, wash I, association; 3: ethynyl-dATP-adenylation, TBTA-catalyzed cycloaddition, wash II, association; 4: ethynyl-dATP-adenylation, TBTA-catalyzed cycloaddition, wash II, association, wash III; 5: THPTA-catalyzed cycloaddition, wash I, association; 6: THPTA-catalyzed cycloaddition, wash I, association, wash III; 7: THPTA-catalyzed cycloaddition, wash II, association; 8: THPTA-catalyzed cycloaddition, wash II, association, wash III. A detailed description of the experiment is provided in Example 5.

FIG. 10 shows an agarose gel with the following lanes: M=RNA ladder; lane 1=RNA obtained using template DNA coupled at its 3' end of the coding strand; lane 2=RNA obtained using template DNA coupled at its 3' end of the non-coding strand (template strand); lane 3=RNA obtained using template DNA coupled at both 3' ends. Further details of the experiment are provided in Example 7.

FIG. 11 shows an exemplary scheme of a linear double-stranded DNA coupled at the 3' end of the non-coding strand to a support (or tag, see below), indicating also the RNA polymerase promoter sequence element and the coding sequence element. The coupling to a support may optionally be via a tag coupled to the 3' end of the non-coding strand, wherein the tag interacts with the support. The numbering is as follows: (16) linear double stranded DNA; (17) coding strand (non-template strand); (18) non-coding strand (template strand); (19) coding sequence element encoded by the coding strand in the direction of from 5' to 3' of the coding strand (here exemplary shown with ATG—accordingly, there is TAC on the non-coding strand in the direction of from 3' to 5' of the non-coding strand); (20) RNA polymerase promotor sequence element; (21) coupling of the non-coding strand at its 3' end; (1) support or tag.

DEFINITIONS

Figure 1:
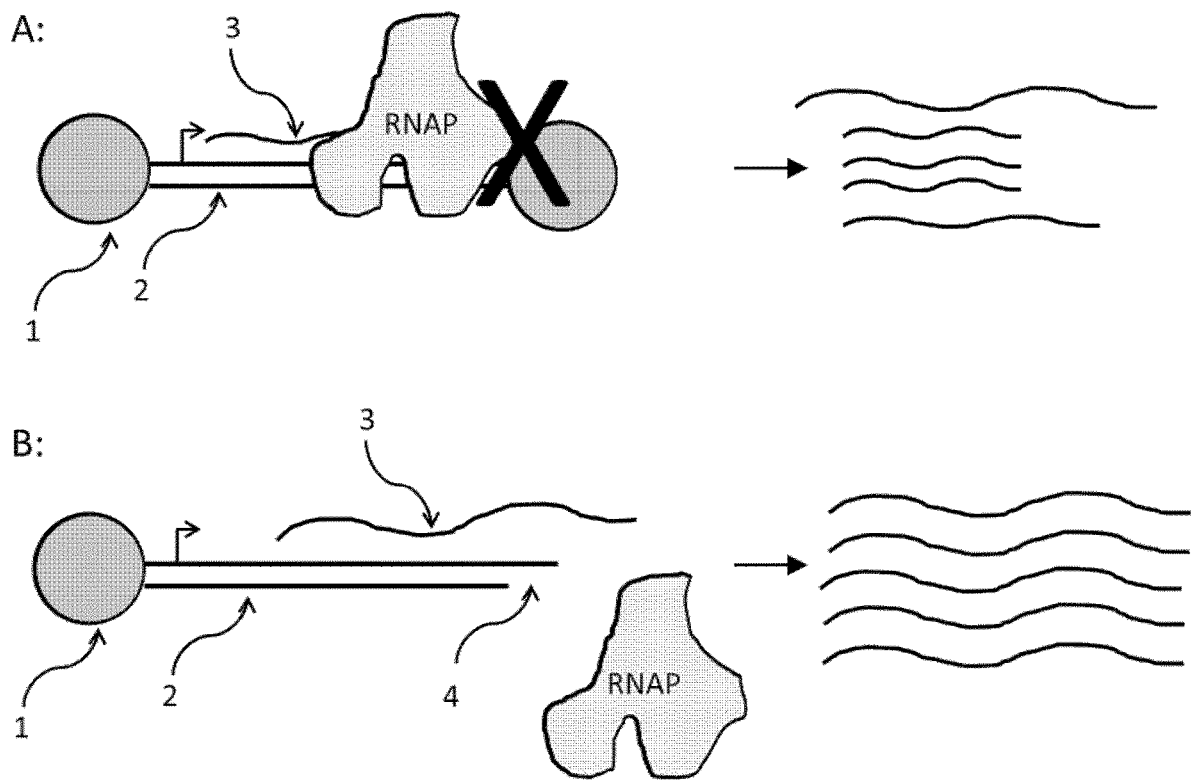
FIG. 1: RNA In Vitro Transcription Using Directed or Undirected Coupling
Figure 2:
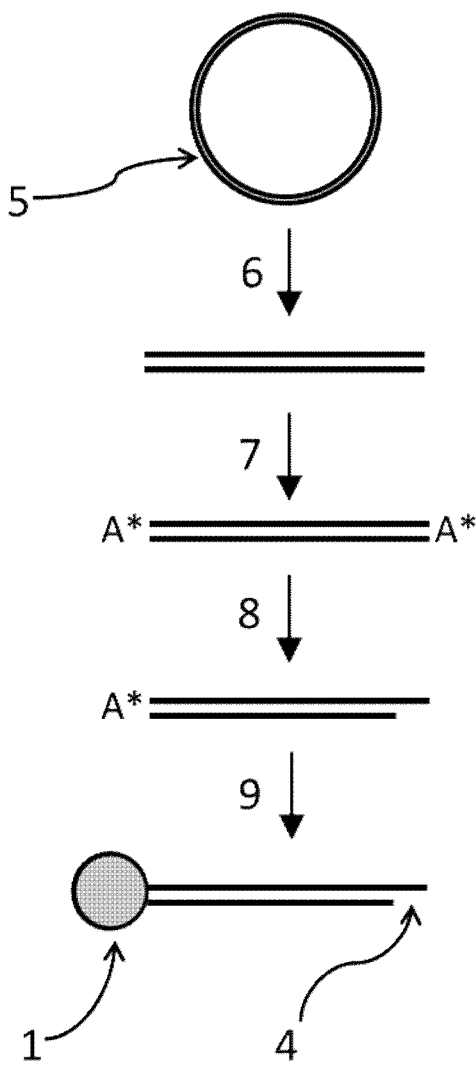
FIG. 2: Exemplary Illustration of a Method Producing Linear Double Stranded DNA According to the Invention
Figure 3:
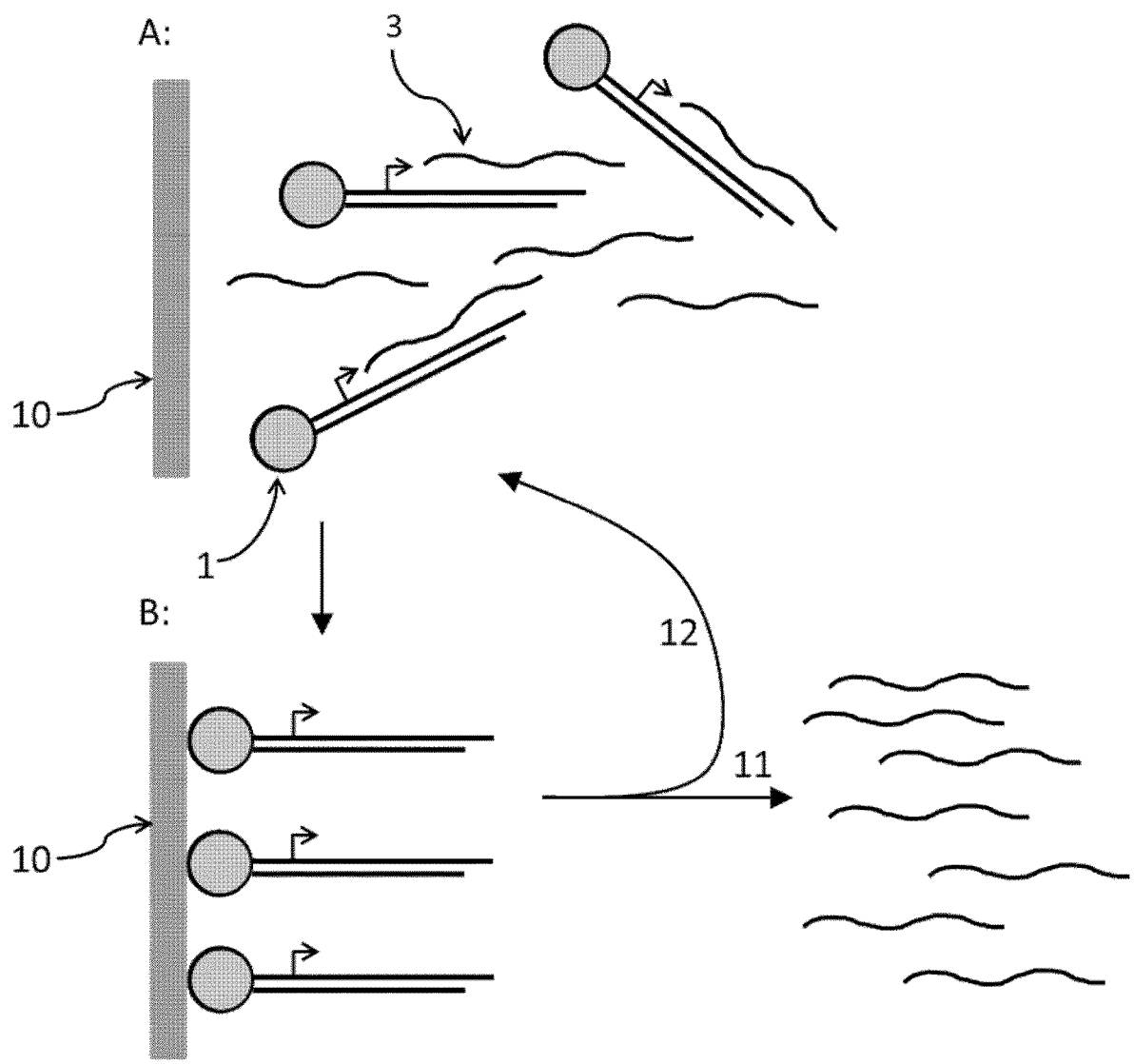
FIG. 3: RNA In Vitro Synthesis Using Linear Double Stranded DNA Associated with a Magnetic Bead Via the 3' End of its Non-Coding Strand

For the sake of clarity and readability the following definitions are provided. Any technical feature mentioned for these definitions may be read on each and every embodiment of the invention. Additional definitions and explanations may be specifically provided in the context of these embodiments.

As used in the specification and the claims, the singular forms of "a" and "an" also include the corresponding plurals unless the context clearly dictates otherwise.

The term "about" in the context of the present invention denotes an interval of accuracy that a person skilled in the art will understand to still ensure the technical effect of the feature in question. The term typically indicates a deviation from the indicated numerical value of ±10% and preferably ±5%.

It needs to be understood that the term "comprising" is not limiting. For the purposes of the present invention, the term "consisting of" is considered to be a preferred embodiment of the term "comprising of". If hereinafter a group is defined to comprise at least a certain number of embodiments, this is also meant to encompass a group which preferably consists of these embodiments only.

The term "antioxidant" refers to a molecule which inhibits the oxidation of other molecules.

The term "bioreactor" as used herein refers to a vessel wherein an RNA in vitro transcription reaction is carried out under specified conditions.

The term "buffer" denotes a weak acid or base used to maintain acidity (pH) of a solution near a chosen value after the addition of another acid or base. Hence, the function of a buffer substance is to prevent rapid change in pH when acids or bases are added to the solution.

The term "cap analogue" refers to a non-extendable di-nucleotide that has a cap functionality which means that it facilitates translation or localization and/or prevent degradation of the RNA when incorporated at the 5' end of the RNA. Non-extendable means that the cap analog will be incorporated only at the 5'terminus because it does not have a 5' triphosphate and therefore cannot be extended in the 3' direction by a template-dependent RNA polymerase. Preferably, the cap analog is added with an initial concentration in the range about 1 to 20 mM, 1 to 17.5 mM, 1 to 15 mM, 1 to 12.5 mM, 1 to 10 mM, 1 to 7.5 mM, 1 to 5 mM or 1 to 2.5 mM.

The term "coding strand" (which may also referred to herein as "non-template strand") denotes the DNA strand of a double stranded DNA whose DNA sequence corresponds to the sequence of the RNA transcript that is transcribed from the DNA (except for thymine being replaced by uracil). The direction of the transcription is from 5' to 3' of the coding strand, wherein the "non-coding strand" serves as template in the transcription reaction. In other words, the direction of the transcription is not toward but, to the opposite, away from the support or tag, which is coupled to the 3' end of the non-coding strand.

The term "non-coding strand" (which may also referred to herein as "template strand") as used herein denotes the DNA strand of a double stranded DNA whose DNA sequence is complementary to the sequence of the RNA transcript that is transcribed from the DNA (except for thymine replacing uracil). When serving as template in the reaction underlying the process of transcription, the RNA polymerase proceeds from 3' to 5' of the non-coding strand, resulting in RNA that corresponds from 5' to 3' to the coding strand (except for thymine being replaced by uracil).

The term "coding sequence element" as used herein defines a part of a double stranded DNA comprising a coding and non-coding strand. The coding sequence element is encoded by the coding strand in the direction of from 5' to 3' of the coding strand. This means that the process of transcription of the coding sequence element will result in an RNA transcript that corresponds to the sequence of the coding strand (except for thymine being replaced by uracil). For this process, the non-coding strand serves as template.

An "RNA polymerase promotor sequence element" is a part of a double stranded DNA comprising a promoter for a RNA polymerase. An RNA polymerase promotor sequence element is located upstream of a coding sequence element. In other words, the RNA polymerase promotor sequence element is located 5' of the coding sequence element, wherein the orientation of the coding sequence element is from 5' to 3' of the coding strand. Thus, in still other words, the RNA polymerase promotor sequence element is located, when described from the orientation of the coding strand (which runs in the direction of the transcription, i.e. from a 5' end of the coding sequence element to a 3' end of the coding sequence element), 5' or upstream of the 5' end of the coding sequence element (i.e. the start of the coding sequence element) on the coding strand.

The orientation of the elements on the linear double stranded DNA is as generally well-known when following the direction of the transcription from 5' to 3': the RNA polymerase promotor sequence element is the first element, followed downstream or 3' by the coding sequence element. This will ensure that the RNA polymerase binds to the promotor upstream or 5' of the coding sequence element, which will then be transcribed from its 5' end to the 3' end. Accordingly, the RNA polymerase is directed to the initiation/start region of the transcription by the binding to the promotor.

A linear double stranded DNA comprising a coding strand and a non-coding strand, wherein said DNA comprises (i) a coding sequence element encoded by the coding strand in the direction of from 5' to 3' of the coding strand and (ii) an RNA polymerase promotor sequence element upstream of the coding sequence element may also be referred to as a linear double stranded DNA comprising a coding strand and a non-coding strand, wherein said DNA comprises (i) a coding sequence element encoded by the coding strand in the direction of from 5' to 3' of the coding strand and (ii) an RNA polymerase promotor sequence element upstream (or 5') of the 5' end of the coding sequence element. Yet alternatively, a linear double stranded DNA comprising a coding strand and a non-coding strand, wherein said DNA comprises (i) a coding sequence element encoded by the coding strand in the direction of from 5' to 3' of the coding strand and (ii) an RNA polymerase promotor sequence element upstream of the coding sequence element may also be referred to as a linear double stranded DNA comprising a coding strand and a non-coding strand, wherein said DNA comprises (i) a coding sequence element encoded by the coding strand in the direction of from 5' to 3' of the coding strand and (ii) an RNA polymerase promotor sequence element upstream (or 5') of the start (or 5' end) of the coding strand encoding the coding sequence element.

A "restriction site element" is a part of a double stranded DNA comprising a restriction site for a restriction endonuclease. A restriction site is typically a short, preferably palindromic nucleotide sequence, e.g. with four to eight nucleotides. EcoRI and PvuII digestion for example produces "blunt ends", while XbaI digestion produces "sticky ends".

The term "counterpart" as used herein denotes an object or molecule that binds to a support or a tag in a highly specific manner. Avidin or streptavidin are for example counterparts of biotin which bind biotin in a highly specific manner.

The verb "to couple" and any form of the verb as used herein denotes a covalent bond between the modified deoxynucleotide and the support or tag.

The term "DNA" is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers or analogs thereof which are—by themselves—composed of a sugar moiety (deoxyribose), a base moiety and a phosphate moiety, and polymerize by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single stranded or double stranded. In the double stranded form, the nucleotides of the first strand typically hybridize with the nucleotides of the second strand, e.g. by A/T-base-pairing and G/C-base-pairing. Although double stranded DNA comprises two opposing strands in terms of the 5' to 3' direction of the two single strands present in the double strand, it is common to nevertheless refer to a 5' end and a 3' end of the double stranded DNA, namely if the DNA comprises a coding sequence element that introduces a direction of the transcription into the double stranded DNA (and accordingly also a direction of the translation). Aspect 2D of the present invention for example comprises the following two steps:

(a) providing linear double stranded DNA comprising a coding sequence element encoded by the coding strand, wherein said DNA has a blunt end 5' of said coding element and a sticky end 3' of said coding element;

(b) incubating said DNA with (i) a modified deoxynucleotide and (ii) an enzyme capable of adding said modified deoxynucleotide at a blunt end to the 3' end of a single strand and not at a sticky end in order to provide linear double stranded DNA with a modified deoxynucleotide at the 3' end of the non-coding strand.

Given the above, these two steps may alternatively referred to as follows:

(a) providing linear double stranded DNA comprising a coding sequence element encoded by the coding strand, wherein said DNA has a blunt end 5' (or upstream in terms of the double stranded DNA) of said coding element and a sticky end 3' (or downstream in terms of the double stranded DNA) of said coding element;

(b) incubating said DNA with (i) a modified deoxynucleotide and (ii) an enzyme capable of adding said modified deoxynucleotide at a blunt end (which is in the present case only present upstream of the coding sequence element but of course nevertheless comprised of a 5' end of the coding strand and a 3' end of the non-coding strand) to the 3' end of a single strand (i.e. to the 3' end of the non-coding single strand present at the blunt end—the enzyme is capable of adding the modified deoxynucleotide only to the 3' end of a single strand, not to the 5' end at a blunt end) and not at a sticky end (which is in the present case only present downstream of the coding sequence element) in order to provide linear double stranded DNA with a modified deoxynucleotide at the 3' end of the non-coding strand.

The term "DNA plasmid" refers to a circular nucleic acid molecule, preferably to an artificial nucleic acid molecule. Such plasmid DNA constructs may be storage vectors, expression vectors, cloning vectors, transfer vectors etc. Preferably, a plasmid DNA within the meaning of the present invention comprises in addition to the elements described herein a multiple cloning site, optionally a selection marker, such as an antibiotic resistance factor, a sequence suitable for multiplication of the vector, such as an origin of replication and a sequence suitable for transcription initiation, such as a promotor. Typical plasmid backbones are e.g. pUC19 and pBR322.

The term "DNA polymerase" refers to any enzyme which is capable of transferring and/or incorporating at least one deoxynucleotide to/into a DNA strand. The term DNA polymerase includes DNA polymerases which are capable of transferring and/or incorporating at least one modified deoxynucleotide or tag-linked deoxynucleotide to/into a DNA strand. The term "engineered DNA polymerase" as used herein refers to genetically engineered DNA polymerases with for example modified and/or improved abilities.

The term "dNTP" is as abbreviation for deoxy nucleosid triphosphate. A deoxy nucleoside triphosphate as used herein contains a nitrogenous base bound to deoxyribose which in turn is bound to three phosphate groups.

The term "linear DNA" refers to a DNA that comprises a free 5' end and a free 3' end, which are not linked to each other. A linear DNA in the context of the invention may be obtained by a restriction digest of a circular DNA (e.g. plasmid DNA) or by a restriction digest of a dbDNA. It is particularly preferred that said restriction digest is performed using enzymes that generate at least one blunt end.

The term "magnet" refers to a material or object that produces a magnetic field. An "electromagnet" is a type of magnet which produces the magnetic field by an electrical current. The magnetic field is present when the electrical current is on and is absent when the electrical current is turned off.

A "modified deoxynucleotide" as used herein is to be understood as a non-naturally occurring deoxynucleotide, which bears a chemically reactive group, which is capable of specifically reacting with another chemically reactive group e.g. with another chemically reactive group of a support or a tag.

The term "pyrophosphatase" refers to an acid anhydride hydrolase that hydrolyses diphosphate bonds. In an RNA in vitro transcription reaction it serves to hydrolyze the bonds within the diphosphate released upon incorporation of the nucleoside triphosphate into the nascent RNA chain and thus, enhances yield of RNA in transcription reactions. Preferably, the concentration of the pyrophosphatase is from 1 to 20 units/ml, 1 to 15 units/ml, 1 to 10 units/ml, 1 to 5 units/ml, or 1 to 2.5 units/ml.

The term "ribonuclease inhibitor" refers to an inhibitor which inhibits the action of a ribonuclease which degrades RNA. Preferably, the concentration of the ribonuclease inhibitor is from about 1 to 500 units/ml, 1 to 400 units/ml, 1 to 300 units/ml, 1 to 200 units/ml or 1 to 100 units/ml.

The term "ribonucleosid triphosphate" is abbreviated by NTP and refers to guanosine triphosphate (GTP), adenine trisphosphate (ATP), cytidine triphosphate (CTP) and uridine triphosphate (UTP).

The term "RNA" is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers or analogs thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. The term "RNA" may refer to a molecule or to a molecule species selected from the group consisting of long-chain RNA, coding RNA, non-coding RNA, single stranded RNA (ssRNA), double stranded RNA (dsRNA), linear RNA (linRNA), circular RNA (circRNA), messenger RNA (mRNA), RNA oligonucleotides, small interfering RNA (siRNA), small hairpin RNA (shRNA), antisense RNA (asRNA), CRISPR/Cas9 guide RNAs, riboswitches, immunostimulating RNA (isRNA), ribozymes, aptamers, ribosomal RNA (rRNA), transfer RNA (tRNA), viral RNA (vRNA), retroviral RNA or replicon RNA, small nuclear RNA (snRNA), small nucleolar RNA (snoRNA), microRNA (miRNA), circular RNA (circRNA), and a Piwi-interacting RNA (piRNA).

The term "RNA in vitro production cycle" as used herein refers to one entire RNA transcription reaction from transcription initiation to its termination (e.g. run-off of the RNA polymerase).

Figure 11:
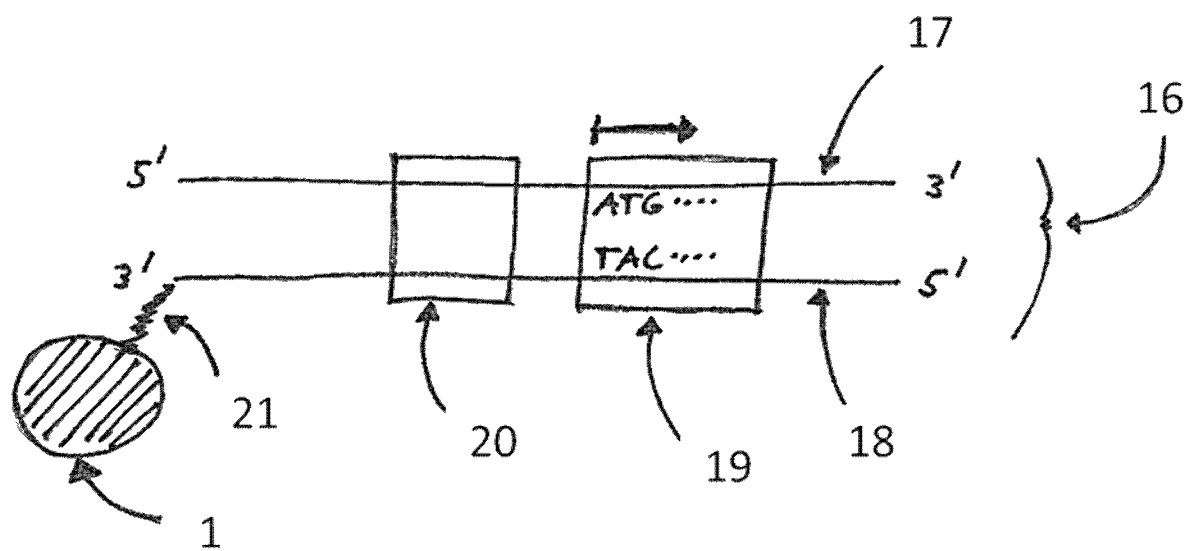
FIG. 11: Schematic Exemplary Drawing of a Linear Double-Stranded DNA According to the Invention

The term "RNA in vitro transcription" relates to a process wherein RNA is synthesized from a DNA template in a cell-free system (in vitro). DNA, preferably a linear DNA (e.g. linearized plasmid DNA, linearized dbDNA), is used as a template for the generation of RNA transcripts. A DNA template for RNA in vitro transcription may be obtained by cloning of a nucleic acid, in particular cDNA corresponding to the respective RNA to be in vitro transcribed, and introducing it into an appropriate vector for RNA in vitro transcription, e.g. into plasmid DNA. In the present invention, the direction of the transcription is away from the support or tag of the underlying linear double stranded DNA template, which is coupled to the 3' end of the non-coding strand, see FIG. 11.

The term "RNA polymerase" refers to any enzyme which catalyzes the transcription of a DNA template into RNA. A "DNA-dependent RNA polymerase" can only catalyze the transcription of RNA from a DNA template. Preferably, the concentration of the DNA-dependent RNA polymerase is from about 1000 to 75000 U/ml, preferably 2500 to 5000 U/ml. Typical DNA-dependent RNA polymerase are T7, SP6, T3 and Syn5 RNA polymerase.

The term "support" as used herein denotes a solid-phase entity including gels. An "activated support" as used herein refers to a support, which bears a chemically reactive group, which is capable of specifically reacting with another chemically reactive group e.g. with another chemically reactive group of a modified deoxynucleotide.

The term "tag" as used herein denotes a moiety, which is capable of binding to or associating with a counterpart. An "activated tag" as used herein refers to a tag, which bears a chemically reactive group, which is capable of specifically reacting with another chemically reactive group e.g. with another chemically reactive group of a modified deoxynucleotide. A "tag-linked deoxynucleotide" as used herein refers to a deoxynucleotide which is covalently bound to a tag as defined above.

The term "UTR" as used herein is the usual abbreviation for "untranslated region". UTRs are typically part of mRNAs and can be located 5' and 3' of the open reading frame of an mRNA. The 5' UTR may be posttranscriptionally modified, for example by addition of a 5' cap. The 5'-UTR may comprise elements for controlling gene expression, which are also called regulatory elements. The 3' UTR may comprise elements which are not encoded in the template, from which an RNA is transcribed, but are added after transcription during maturation, e.g. a poly(N/A) sequence.

The term "Doggybone™" (dbDNA) as used herein denotes a minimal, closed-linear DNA vector enzymatically developed by Touchlight Genetics Ltd. The linear DNA is rapidly produced, plasmid-free and synthesized through an enzymatic process that yields a vector cassette containing only the encoded sequence of interest, promoter, poly A tail and telomeric ends.

DETAILED DESCRIPTION OF THE FINDINGS UNDERLYING THE PRESENT INVENTION

In order to obtain high-quality RNA suitable to be used in RNA-based therapy, it is important to efficiently and reliably remove the DNA template from the final RNA product to ensure efficacy and safety of RNA-based therapeutics.

DNA template removal from RNA in vitro transcription reactions can for example be achieved by enzymatic DNA digestion and purification of the RNA. However, this procedure is rather elaborate, the DNA template is destroyed and bears the risk of residual DNA fragments in the purified RNA. Hence, such an approach is not suitable for RNA production on a large scale. Methods using a DNA template coupled to a single support or tag at the 5' end of its coding strand for separation, have the drawback that they are based on error-prone PCR procedures and are sequence-dependent, which is also not suitable for large-scale RNA production.

The present invention is based on the finding that linear double stranded DNA can be coupled to a support or a tag for separation in a specific manner after the generation of linear DNA.

In contrast to other chemical coupling techniques such as coupling to CnBr-activated sepharose or coupling to $NH_2$ beads via EDC/sulfo-NHS which lead to undirected coupling of the support across the DNA, the methods of the present invention allow for directed coupling of a support or tag, namely at the 3' end of the non-coding strand of a linear double stranded DNA. Specific coupling of a support or tag can for example be achieved via a modified deoxynucleotide at the 3' end of the non-coding strand of a linear double stranded DNA using highly specific and efficient "click" chemistry reactions (e.g. CuAAC, SPAAC or tetrazine-alkene ligation).

Directed coupling of a single support or tag according to the invention leaves the linear double stranded DNA accessible to enzymatic reactions (e.g. restriction digestion or RNA in vitro transcription) while undirected coupling prevents accessibility of enzymes. With regard to RNA in vitro transcription, undirected coupling is further likely to block efficient run-off of the RNA polymerase leading to an inhomogeneous RNA product pool.

Moreover, directed coupling according to the invention comprises no sequence specific steps such as the use of sequence-specific primers and error-prone steps such as PCR.

Figure 4:
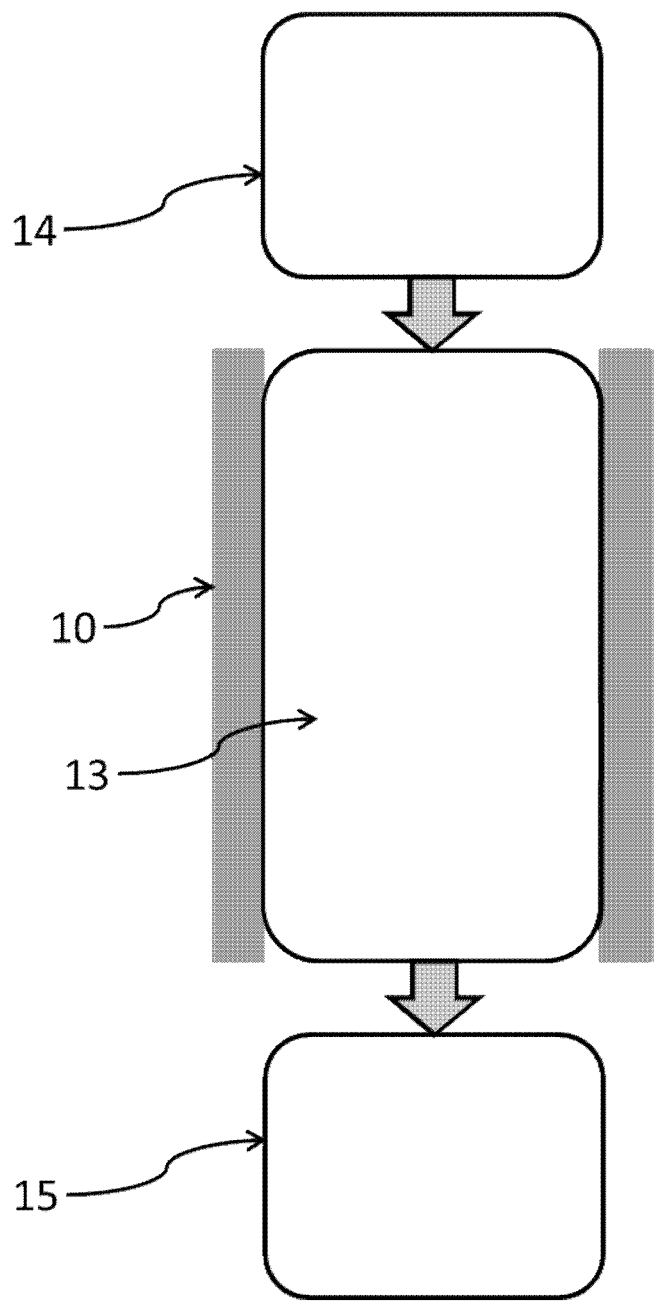
FIG. 4: Bioreactor for RNA In Vitro Transcription

Thus, the present invention provides high-quality linear double stranded DNA coupled to a support or a tag, which can serve as a template for enzymatic reactions, in particular RNA in vitro transcriptions, and can easily and efficiently be recovered and recycled (see FIG. 4).

The present invention further provides methods for producing said high-quality linear double stranded DNA.

The inventors realized that the underlying principle of the coupling strategy of the invention may not only be exploited in large scale RNA production but is broadly applicable to diverse enzymatic reactions (e.g. DNA amplification reactions) and applications (DNA detection e.g. on a DNA chip) involving linear double stranded DNA.

PREFERRED EMBODIMENTS OF THE PRESENT INVENTION

In the following, further preferred embodiments of the present invention are described.

1. A linear double stranded DNA comprising a coding strand and a non-coding strand, wherein said DNA comprises (i) a coding sequence element encoded by the coding strand in the direction of from 5' to 3' of the coding strand and (ii) an RNA polymerase promotor sequence element upstream of the coding sequence element, wherein said non-coding strand is coupled at its 3' end to a support or a tag, and wherein said support or tag is the only support or tag coupled to said DNA.

2. The linear double stranded DNA according to embodiment 1, wherein said tag is biotin, preferably associated with streptavidin, more preferably a streptavidin coated bead, most preferably a streptavidin coated magnetic bead.

3. A method for producing linear double stranded DNA comprising a coding strand and a non-coding strand, wherein said non-coding strand is coupled at its 3' end to a support or a tag, comprising the steps of:
    (a) providing linear double stranded DNA comprising a coding sequence element encoded by the coding strand, followed at the 3' end by a restriction site element;
    (b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
    (c) incubating the DNA obtained in step (b) with a restriction endonuclease recognizing said restriction site element in order to obtain linear double stranded DNA with a modified deoxynucleotide at the 3' end of the non-coding strand;
    (d) coupling the DNA obtained in step (c) via its modified deoxynucleotide to a support or a tag in order to provide linear double stranded DNA, wherein the non-coding strand of said DNA is coupled at its 3' end to a support or a tag.

4. The method according to embodiment 3, wherein the enzyme capable of adding a modified deoxynucleotide at the 3' end of a strand in step (b) is a DNA polymerase, preferably a *Thermus aquaticus* DNA polymerase.

5. The method according to embodiments 3 or 4, wherein the support is selected from the group consisting of a magnetic bead, a nanoparticle, agarose, glass, poly(methyl methacrylate), a microchip, sepharose, sephadex and silica and wherein the tag is selected from the group consisting of biotin and PEG.

6. The method according to any one of embodiments 3 to 5, wherein the support or the tag used in the coupling step is an activated support or an activated tag.

7. The method according to embodiment 6, wherein the modified deoxynucleotide is an alkyne deoxynucleotide and wherein the activated support or tag is an azide-activated support or tag.

8. The method according to embodiment 7, wherein the modified deoxynucleotide is an ethynyl-dNTP and wherein the activated support or tag is an azide-activated support or tag.

9. The method according to embodiment 8, wherein the modified deoxynucleotide is an ethynyl-dATP and wherein the activated tag is an azide-activated biotin.

10. A method for producing linear double stranded DNA comprising a coding strand and a non-coding strand, wherein said non-coding strand is coupled at its 3' end to a tag, comprising the steps of:
    (a) providing linear double stranded DNA comprising a coding sequence element encoded by the coding strand, followed at the 3' end by a restriction site element;
    (b) incubating said DNA with (i) a tag-linked deoxynucleotide and (ii) an enzyme capable of adding a tag-linked deoxynucleotide at a 3'end of a strand in order to provide linear double stranded DNA with a tag-linked deoxynucleotide at the 3' end of each strand;

(c) incubating the DNA obtained in step (b) with a restriction endonuclease recognizing said restriction site element in order to obtain linear double stranded DNA, wherein the non-coding strand of said DNA is coupled at its 3' end to a tag.

11. The method according to embodiment 10, wherein the tag-linked deoxynucleotide is selected from the group consisting of a biotin-deoxynucleotide and a PEG-deoxynucleotide, preferably a biotin-deoxynucleotide.

12. The method according to embodiment 10 or 11, wherein the enzyme capable of adding a tag-linked deoxynucleotide at the 3' end of a strand in step (b) is selected from the group of *Thermus aquaticus* DNA polymerase and terminal transferase.

13. A method for producing RNA in vitro comprising the steps of:
    (a) providing the double stranded linear DNA according to any one of embodiments 1 to 2 as template DNA;
    (b) providing (i) ribonucleoside triphosphates and (ii) a DNA-dependent RNA polymerase;
    (c) incubating the DNA provided in step (a) with (i) and (ii) provided in step (b) under suitable conditions in order to produce RNA.

14. The method according to embodiment 13, wherein the DNA-dependent RNA polymerase is a bacteriophage RNA polymerase, preferably a T3, T7 or SP6 DNA-dependent RNA polymerase.

15. The method according to embodiment 13 or 14, wherein the DNA provided in step (a) is re-used in at least one further RNA in vitro production cycle.

Still further preferred embodiments of the present invention are indicated in the following.

1. A linear double stranded DNA comprising a coding strand and a non-coding strand, wherein said DNA comprises a coding sequence element encoded by the coding strand, wherein said non-coding strand is coupled at its 3' end to a support or a tag, and wherein said support or tag is the only support or tag coupled to said DNA.

2. The linear double stranded DNA according to embodiment 1, wherein said non-coding strand is coupled at its 3' end to a support or a tag via a triazole.

3. The linear double stranded DNA according to embodiment 1 or 2, wherein said tag is biotin.

4. The linear double stranded DNA according to embodiment 3, wherein said biotin is associated with streptavidin, preferably a streptavidin coated bead, most preferably a streptavidin coated magnetic bead.

5. The linear double stranded DNA according to any one of embodiments 1 to 4, wherein the coding sequence element is flanked by a 5' UTR and/or a 3' UTR element.

6. The linear double stranded DNA according to any one of embodiments 1 to 5, wherein said DNA comprises 5' of the coding sequence element an RNA polymerase promotor sequence element.

7. A method for producing linear double stranded DNA comprising a coding strand and a non-coding strand, wherein said non-coding strand is coupled at its 3' end to a support or a tag, comprising the steps of:
    (a) providing linear double stranded DNA comprising a coding sequence element encoded by the coding strand, followed at the 3' end by a restriction site element;
    (b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
    (c) incubating the DNA obtained in step (b) with a restriction endonuclease recognizing said restriction site element in order to obtain linear double stranded DNA with a modified deoxynucleotide at the 3' end of the non-coding strand;
    (d) coupling the DNA obtained in step (c) via its modified deoxynucleotide to a support or a tag in order to provide linear double stranded DNA, wherein the non-coding strand of said DNA is coupled at its 3' end to a support or a tag.

8. A method for producing linear double stranded DNA comprising a coding strand and a non-coding strand, wherein said non-coding strand is coupled at its 3' end to a support or a tag, comprising the steps of:
    (a) providing linear double stranded DNA comprising a coding sequence element encoded by the coding strand, followed at the 3' end by a restriction site element;
    (b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
    (c) coupling the DNA obtained in step (b) via the modified deoxynucleotide at the 3' end of each strand to a support or a tag;
    (d) incubating the DNA obtained in step (c) with a restriction endonuclease recognizing said restriction element in order to provide linear double stranded DNA, wherein the non-coding strand of said DNA is coupled at its 3' end to a support or a tag.

9. The method according to embodiment 7 or 8, wherein the modified deoxynucleotide is selected from the group consisting of an alkyne deoxynucleotide, an azide deoxynucleotide, an azadibenzocyclooctyne deoxynucleotide, a trans-cyclooctene deoxynucleotide, and a vinyl deoxynucleotide.

10. The method according to any one of embodiments 7 to 9, wherein the enzyme capable of adding a modified deoxynucleotide at the 3' end of a strand in step (b) is a DNA polymerase.

11. The method according to embodiment 10, wherein the DNA polymerase is selected from the group consisting of a *Thermus aquaticus* DNA polymerase, an *Escherichia coli* DNA polymerase, a *Saccharomyces cerevisiae* DP1 DNA polymerase, a mammalian DNA 13 polymerase, an engineered DNA polymerase, a DNA polymerase I large (Klenow) fragment and a terminal transferase.

12. The method according to embodiment 11, wherein the DNA polymerase is a *Thermus aquaticus* DNA polymerase and wherein the linearized DNA provided in step (a) comprises a blunt end at the 5' end of the coding sequence element.

13. The method according to any one of embodiments 7 to 12, wherein the support is selected from the group consisting of a magnetic bead, a nanoparticle, agarose, glass, poly(methyl methacrylate), a microchip, sepharose, sephadex and silica and wherein the tag is selected from the group consisting of biotin and PEG.

14. The method according to any one of embodiments 7 to 13, wherein the support or the tag used in the coupling step is an activated support or an activated tag.

15. The method according to embodiment 14, wherein the activated support or tag is selected from the group consisting of an alkyne-activated support or tag, an azide-activated support or tag, an azadibenzocyclooctyne-activated support or tag, a tetrazine-activated support or tag, and a trans-cyclooctene-activated support or tag.

16. The method according to embodiment 14 or 15, wherein the modified deoxynucleotide is coupled to the activated support or tag via CuAAC, SPAAC or tetrazine-alkene ligation.
17. The method according to any one of embodiments 14 to 16, wherein the modified deoxynucleotide is an alkyne deoxynucleotide and wherein the activated support or tag is an azide-activated support or tag.
18. The method according to any one of embodiments 14 to 16, wherein the modified deoxynucleotide is an azide deoxynucleotide and wherein the activated support or tag is an alkyne-activated support or tag.
19. The method according to any one of embodiments 14 to 16, wherein the modified deoxynucleotide is an azadibenzocyclooctyne deoxynucleotide and wherein the activated support or tag is an azide-activated support or tag.
20. The method according to any one of embodiments 14 to 16, wherein the modified deoxynucleotide is an azide deoxynucleotide and wherein the activated support or tag is an azadibenzocyclooctyne-activated support or tag.
21. The method according to any one of embodiments 14 to 16, wherein the modified deoxynucleotide is a trans-cyclooctene deoxynucleotide and wherein the activated support or tag is a tetrazine-activated support or tag.
22. The method according to any one of embodiments 14 to 16, wherein the modified deoxynucleotide is a vinyl deoxynucleotide and wherein the activated support or tag is a tetrazine-activated support or tag.
23. The method according to any one of embodiments 14 to 16, wherein the modified deoxynucleotide is an ethynyl-dNTP and wherein the activated support or tag is an azide-activated support or tag.
24. The method according to embodiment 23, wherein the modified deoxynucleotide is an ethynyl-dATP and wherein the activated tag is an azide-activated biotin.
25. The method according to embodiment 23 or 24, wherein the coupling step is carried out in the presence of Cu(I).
26. The method according to embodiment 25, wherein the coupling step is performed in the presence of Cu(I)-TBTA or Cu(I)-THPTA.
27. The method according to embodiment 25 or 26, wherein an additional washing step is performed in order to remove Cu(I) via complexation to EDTA after the coupling step.
28. The method according to any one of embodiments 7 to 27, wherein said method comprises an additional step after the step where said DNA is incubated with a restriction endonuclease, namely an additional step of separating the linear double stranded DNA with a modified deoxynucleotide or with a support or a tag at the 3' end of the non-coding strand from linear double stranded DNA with a modified deoxynucleotide or with a support or a tag at the 3' end of the coding strand.
29. The method according to embodiment 28, wherein said separating is achieved via size of the DNA, preferably using AMPure XP beads.
30. The method according to any one of embodiments 7 to 29, wherein the restriction site element is an EcoRI site and wherein the restriction endonuclease is EcoRI.
31. A method for producing linear double stranded DNA comprising a coding strand and a non-coding strand, wherein said non-coding strand is coupled at its 3' end to a tag, comprising the steps of:
    (a) providing linear double stranded DNA comprising a coding sequence element encoded by the coding strand, followed at the 3' end by a restriction site element;
    (b) incubating said DNA with (i) a tag-linked deoxynucleotide and (ii) an enzyme capable of adding a tag-linked deoxynucleotide at a 3'end of a strand in order to provide linear double stranded DNA with a tag-linked deoxynucleotide at the 3' end of each strand;
    (c) incubating the DNA obtained in step (b) with a restriction endonuclease recognizing said restriction site element in order to obtain linear double stranded DNA, wherein the non-coding strand of said DNA is coupled at its 3' end to a tag.
32. The method according to embodiment 31, wherein the tag-linked deoxynucleotide is selected from the group consisting of a biotin-deoxynucleotide and a PEG-deoxynucleotide.
33. The method according to embodiment 31 or 32, wherein the enzyme capable of adding a tag-linked deoxynucleotide at the 3' end of a strand in step (b) is selected from the group of *Thermus aquaticus* DNA polymerase and terminal transferase.
34. The method according to any one of embodiments 30 to 33, wherein said method comprises an additional step after the step where said DNA is incubated with a restriction endonuclease, namely an additional step of separating the linear double stranded DNA with a tag-linked deoxynucleotide at the 3' end of the non-coding strand from linear double stranded DNA with a tag-linked deoxynucleotide at the 3' end of the coding strand.
35. The method according to embodiment 34, wherein said separating is achieved via size of the DNA, preferably using AMPure XP beads.
36. The method according to any one of embodiments 31 to 35, wherein the restriction site element is an EcoRI site and wherein the restriction endonuclease is EcoRI.
37. A method for producing linear double stranded DNA comprising a coding strand and a non-coding strand, wherein said non-coding strand is coupled at its 3' end to a support or a tag, comprising the steps of:
    (a) providing linear double stranded DNA comprising a coding sequence element encoded by the coding strand, wherein said DNA has a blunt end 5' of said coding element and a sticky end 3' of said coding element;
    (b) incubating said DNA with (i) a modified deoxynucleotide and (ii) an enzyme capable of adding said modified deoxynucleotide at a blunt end to the 3' end of a single strand and not at a sticky end in order to provide linear double stranded DNA with a modified deoxynucleotide at the 3' end of the non-coding strand;
    (c) coupling the DNA obtained in step (b) via its modified deoxynucleotide to a support or a tag in order to provide linear double stranded DNA, wherein the non-coding strand of said DNA is coupled at its 3' end to a support or a tag.
38. A method for producing linear double stranded DNA comprising a coding strand and a non-coding strand, wherein said non-coding strand is coupled at its 3' end to a tag, comprising the steps of:
    (a) providing linear double stranded DNA comprising a coding sequence element encoded by the coding strand, wherein said DNA has a blunt end 5' of said coding element and a sticky end 3' of said coding element;
    (b) incubating said DNA with (i) a tag-linked deoxynucleotide and (ii) an enzyme capable of adding a tag-linked deoxynucleotide at a blunt end to the 3' end of a single strand and not at a sticky end in order to provide linear double stranded DNA with a tag-linked deoxynucleotide at the 3' end of the non-coding strand.

39. The method according to embodiment 37 or 38, wherein the enzyme capable of adding a modified deoxynucleotide or a tag-linked deoxynucleotide at a blunt end to the 3' end of a single strand is *Thermus aquaticus* DNA polymerase.
40. Use of the linear double stranded DNA according to any one of embodiments 1 to 6 in an RNA in vitro transcription reaction.
41. A method for producing RNA in vitro comprising the steps of:
    (a) providing the double stranded linear DNA according to any one of embodiments 1 to 6 as template DNA;
    (b) providing (i) ribonucleoside triphosphates and (ii) a DNA-dependent RNA polymerase;
    (c) incubating the DNA provided in step (a) with (i) and (ii) provided in step (b) under suitable conditions in order to produce RNA.
42. The method according to embodiment 41, wherein the DNA-dependent RNA polymerase is a bacteriophage RNA polymerase, preferably a T3, T7 or SP6 DNA-dependent RNA polymerase.
43. The method according to embodiment 41 or 42, wherein a cap analogue is additionally provided in step (b).
44. The method according to any one of embodiments 41 to 43, wherein a ribonuclease inhibitor is additionally provided in step (b).
45. The method according to any one of embodiments 41 to 44, wherein pyrophosphatase is additionally provided in step (b).
46. The method according to any one of embodiments 41 to 45, wherein $MgCl_2$ is additionally provided in step (b).
47. The method according to any one of embodiments 41 to 46, wherein the DNA is incubated in step (c) in a buffer suitable for producing RNA in vitro.
48. The method according to any one of embodiments 41 to 47, wherein the DNA provided in step (a) is re-used in at least one further RNA in vitro production cycle.
49. A bioreactor for RNA in vitro transcription comprising
    (a) a reaction vessel (13) comprising the linear double stranded DNA according to any one of embodiments 1 to 6;
    (b) a vessel (14) comprising ribonucleoside triphosphates and DNA-dependent RNA polymerase, wherein said vessel is connected to the reaction vessel; and
    (c) a product vessel (15) for collecting the RNA product, wherein said vessel is also connected to the reaction vessel.
50. The bioreactor according to embodiment 49, wherein the reaction vessel (13) comprises the linear double stranded DNA associated with a streptavidin coated magnetic bead according to embodiment 4.
51. The bioreactor according to embodiment 50, wherein a magnet is surrounding the reaction vessel (13) from the outside.
52. The bioreactor according to embodiment 51, wherein the magnet is capable of oscillating in order to mix a reaction mixture comprising said linear double stranded DNA.
53. The bioreactor according to embodiment 51 or 52, wherein the magnet is capable of attracting the linear double stranded DNA in order to separate it from the RNA product, which may be collected in the product vessel (15).
54. The bioreactor according to embodiment 49, wherein the support or the tag of the linear double stranded DNA according to any one of embodiments 1 to 6 is linked to said reaction vessel (13).
55. The bioreactor according to any one of embodiments 49 to 54, wherein the vessel (14) further comprises at least one of the following independently selected from the group consisting of a buffer suitable for in vitro transcription, a cap analogue, modified ribonucleoside triphosphates, a ribonuclease inhibitor, a pyrophosphatase, $MgCl_2$, an antioxidant and a polyamine.
56. The bioreactor according to any one of embodiments 49 to 55, wherein the reaction vessel (13) comprises at least one means for measuring and/or adjusting pH, salt concentration, magnesium concentration, phosphate concentration, temperature, pressure, flow velocity, RNA concentration and/or ribonucleotide triphosphate concentration.
57. The bioreactor according to any one of embodiments 49 to 56, wherein the bioreactor comprises a filtration membrane between the reaction vessel (13) and the product vessel (15), preferably an ultrafiltration membrane for separating the RNA product from the reaction mix.
58. The bioreactor according to embodiment 57, wherein the filtration or ultrafiltration membrane has a molecular cut-off in a range from 10 to 100 kDa, 10 to 75 kDa, 10 to 50 kDa, 10 to 25 kDa or 10 to 15 kDa.
59. The bioreactor according to embodiment 57 or 58, wherein the filtration or ultrafiltration membrane is selected from the group consisting of regenerated cellulose, modified cellulose, polysulfone, polyethersulfone, polyacrylonitrile, polymethylmethacrylate, polyvinyl alcohol and polyarylethersulfone.
60. The bioreactor according to any one of embodiments 49 to 59, wherein the product vessel (15) comprises a resin to capture the produced RNA and in order to separate the RNA product from other soluble components of the reaction mix.
61. The bioreactor according to any one of embodiments 49 to 60, wherein said bioreactor operates in a batch, semi-batch or in a continuous mode.
62. Use of the bioreactor according to any one of embodiments 49 to 61 in a method according to any one of embodiments 41 to 48.
63. A kit comprising
    (a) a modified deoxynucleotide;
    (b) a *Thermus aquaticus* DNA polymerase capable of adding said modified deoxynucleotide to the 3' end of a strand at a blunt DNA end;
    (c) an activated support or tag;
    (d) a counterpart of said support or tag associating in a highly specific manner with said support or tag.
64. A kit comprising
    (a) a tag-linked deoxynucleotide;
    (b) a *Thermus aquaticus* DNA polymerase capable of adding said tag-linked deoxynucleotide to the 3' end of a strand at a blunt DNA end;
a counterpart of said tag associating in a highly specific manner with said tag.

EXAMPLES

The following Examples are merely illustrative and shall describe the present invention in a further way. These Examples shall not be construed to limit the present invention thereto.

Example 1: Coupling of Linearized DNA to CnBr-Activated Sepharose

The aim of this example was to find out whether linearized DNA can be coupled to CnBR-activated sepharose and if so, whether said DNA is still accessible to enzymatic reactions.

1 µg of plasmid DNA (SEQ ID NO: 1) was linearized using either 10 U XbaI to generate sticky DNA ends or 10 U PvuII to generate blunt DNA ends. The restriction reaction was performed in 20 µl 1× restriction buffer at 37° C. for 1 hour. Subsequently, the reaction was analyzed on a 0.8% agarose gel by agarose gel electrophoresis to ensure complete linearization. Linear DNA was purified using AMPure XP beads (Beckman coulter) according to the manufacturer's instructions.

Figure 5:
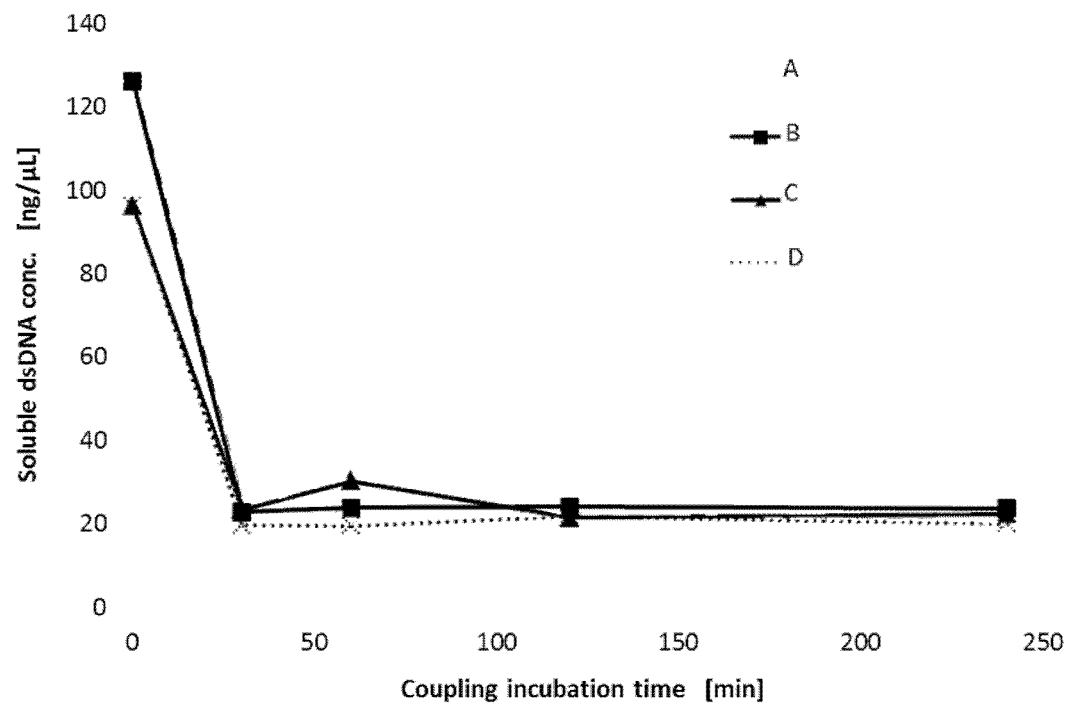
FIG. 5: Coupling of Linearized Plasmid DNA to Sepharose

The coupling of XbaI- or PvuII-linearized DNA on CnBr-activated 4B or 6 MB sepharose (GE Healthcare) was performed according to the manufacturer's instructions. In brief, 4B or 6 MB sepharose was suspended, allowed to swell in 1 mM HCl and subsequently washed. For coupling, sepharose was re-suspended in coupling buffer (0.1 M $NaHCO_3$ pH 8.3 containing 0.5 M NaCl) and XbaI- or PvuII-linearized DNA and incubated at room temperature. In order to monitor DNA coupling to sepharose, the coupling reaction was centrifuged and fractions were taken from the supernatant at 0.5, 1, 2 and 4 hours and analyzed for the presence of free soluble DNA (see FIG. 5). After 4 hours, the coupling reaction was washed in coupling buffer for 4 hours. The sepharose-coupled linear DNA was blocked in 0.1 M Tris-HCl (pH 8, 1 mM EDTA) at room temperature for 2 hours, washed three times (washing cycle 1: coupling buffer; washing cycle 2: 0.1 M acetate) and finally stored in 1M NaCl buffer at 2-8° C.

Analysis of the supernatants from centrifugation at 0.5, 1, 2 and 4 hours revealed that coupling of linear DNA was independent of the linearization mode (sticky or blunt ends) and the type of sepharose bead (4B or 6 MB). 80% of DNA were coupled within 30 minutes. Furthermore, stringent washing using coupling buffer and 0.1 M acetate did not lead to a release of DNA from the sepharose beads (data not shown).

Following successful coupling, aliquots of about 1 µg of coupled DNA from the 30 minute and 2 hours time point were digested using 10 U EcoRI for 1 hour. The reaction was stopped by heating the digestion up to 65° C. for 15 minutes. The reaction was centrifuged to pellet sepharose-coupled linear DNA and the supernatant was analyzed for digested, free DNA on a 1% agarose gel by agarose gel electrophoresis. (FIG. 6A).

The agarose gel did not show the DNA fragments, which were expected upon EcoRI digestion of the sepharose-coupled DNA samples. A positive control for EcoRI treatment can be found in lane 3 of FIG. 6A. The fact that sepharose-coupled DNA could not be digested by restriction enzymes suggested that the sepharose-immobilized DNA was no longer accessible due to strong and unspecific/undirected binding of the DNA to sepharose.

In order to test whether other enzymatic reaction were impaired as well, RNA in vitro transcription was performed using XbaI- or PvuII-linearized 4B- or 6 MB sepharose-coupled DNA, T7 RNA polymerase and sequence optimized Cap/NTP mix at 37° C. for 2 hours. The reaction was stopped using 40 mM EDTA and purified using AMPure XP beads.

Figure 6:
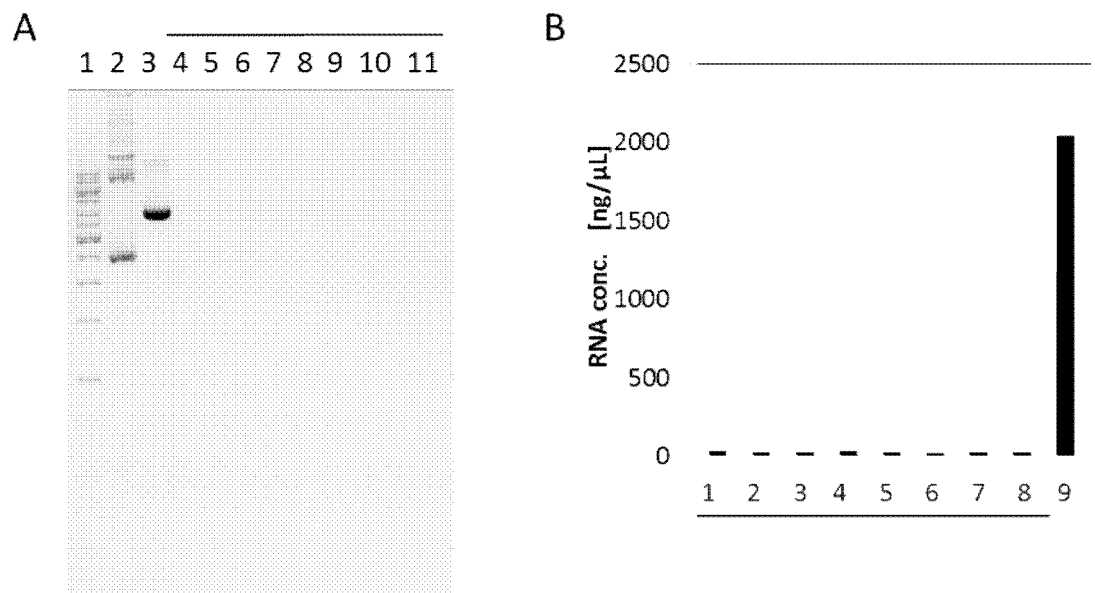
FIG. 6: Restriction Digest and RNA In Vitro Transcription of Sepharose-Coupled Linear DNA FIG. 6A Agarose gel showing: lane 1=DNA-ladder; lane 2=undigested circular plasmid DNA; 3=free pDNA treated with EcoRI; 4,5=XbaI-linearized 6 MB sepharose-coupled DNA; 6, 7=XbaI-linearized 4B sepharose-coupled DNA; 8, 9=PvuII-linearized 6 MB sepharose-coupled DNA; 10, 11=PvuII-linearized 4B sepharose-coupled DNA.

Product RNA could not be detected in any of the RNA in vitro transcription reactions while product RNA was observed for the non-coupled linearized plasmid DNA (FIG. 6B). In addition to the negative results obtained for the enzymatic digestion, the negative results for the in vitro transcription confirm that sepharose-coupled linear DNA is no longer accessible to enzymatic reactions.

Example 2: Coupling of Linearized DNA to NH2 Beads Using EDC/Sulfo-NHS

The aim of this example was to find out whether linearized DNA which is coupled to $NH_2$ beads using EDC sulfo-NHS is still accessible to enzymatic reactions.

1 mg plasmid DNA (SEQ ID NO: 1) was linearized using 500 U PvuII to generate blunt DNA ends. The restriction reaction was performed in 5 ml 1× restriction buffer at 37° C. for 2 hours. The resulting blunt DNA ends were dephosphorylated for 30 minutes at 37° C. using 300 U alkaline phosphatase to prevent re-ligation. The phosphatase reaction was stopped by adding 0.1% SDS for 10 minutes at 65° C. Afterwards, the linearized and dephosphorylated DNA was washed with 1 ml ice cold propanol and centrifugated at 20,000 g for 20 minutes at room temperature. The pellet was dried for 10 to 30 minutes. Then the DNA was further digested with AseI for 2 hours at 37° C. to generate carboxylate groups, which are mandatory for coupling to $NH_2$-beads via EDC/sulfo-NHS and subsequently washed with isopropanol as described above. Finally, PvuII/AseI-digested DNA was dissolved in 2× coupling buffer and the DNA concentration was determined using Nanodrop2000.

16 mg EDC and 44 mg sulfo-NHS were dissolved in 100 µl wfi (water for injection) prior to mixing with PvuII/AseI-digested DNA as a 20× solution. 1 g $NH_2$-beads were washed 3 times using 2 ml MES coupling buffer (0.2 M 2-Morpholinoethanesulfonic Acid, pH 6; 1 M NaCl) in a 0.2 µm Vivaspin-2 column (20.000 g, 1 min). In order to couple PvuII/AseI-digested DNA, 5 µl of 20×EDC and 20× sulfo-NHS were added to 100 µg DNA in 40 µl wfi to a final volume of 50 µl and incubated for 15 minutes to activate 5'-phosphate groups of the DNA. 0.14 µl 2-mercaptoethanol was subsequently added to inactivate excess EDC. Afterwards, 100 µl $NH_2$-beads were added and the reaction was incubated for 1.5 to 3 hours at room temperature. Finally, the reaction was terminated by 10 mM hydroxylamine or 100 mM Tris-HCl, pH 8 for 30 minutes at room temperature.

In order to test whether the $NH_2$-coupled DNA was accessible to enzymatic reactions and could be digested using restriction endonucleases, the $NH_2$-coupled DNA was digested by EcoRI and analyzed by agarose gel electrophoresis as described in Example 1.

The agarose gel did not show the DNA fragments, which were expected upon EcoRI digestion of the $NH_2$-coupled DNA (data not shown). The fact that $NH_2$-coupled DNA cannot be digested by restriction enzymes suggests that the sepharose-immobilized DNA is no longer accessible due to strong and unspecific/undirected binding of the DNA to $NH_2$ beads.

Attempts of RNA in vitro transcription likewise failed (data not shown). In addition to the negative results obtained for the enzymatic digest, the negative results for the RNA in vitro transcription confirms that $NH_2$-coupled linear DNA is no longer accessible to enzymatic reactions.

Example 3: Coupling of Linearized DNA to Azide-Biotin Via Cu(I)-Catalyzed Azide-Alkyne Cycloaddition (CuAAC) and Subsequent Association with Magnetic Streptavidin Beads The aim of this example was to find out whether linearized plasmid DNA can be coupled to azide-biotin via CuAAC (so called "click" reaction) and can be further associated to streptavidin beads and if so, whether said DNA is still accessible to enzymatic reactions.

1 mg of plasmid DNA (SEQ ID NO: 1) was linearized using 200 U PvuII for 2 hour at 37° C. and 600 rpm to generate blunt DNA ends. The linearized DNA was purified using AMPure XP beads and the restriction reaction was analyzed via agarose gel electrophoresis as described in Example 1.

Alkyne moieties which react to azide-biotin and enable association of the linearized DNA with streptavidin were generated by adenylating 300 µg of linearized DNA with 40 µM 7-ethynyl-dATP and 1 U Taq-polymerase for 55 minutes at 72° C. and 1000 rpm. Adenylation using dATP was performed as a negative control as this reaction does not generate alkyne moieties. Adenylation via *Thermus aquaticus* (Taq) polymerase takes place at the 3' end of each strand of a double stranded linearized DNA. The adenylation reaction was subsequently purified using AMPure XP beads. In order to obtain linear double stranded DNA with an 7-ethynyl-dATP only on the 3' end of the template strand, the linearized adenylated DNA was digested using EcoRI for 60 minutes at 37° C. and 100 rpm and again purified using AMPure XP beads.

Cu(I)-catalyzed azide-alkyne cycloaddition of 7-ethynyl-dATP of the DNA with the azide group of an azide-biotin was performed using BaseClick-Kit biotin (baseclick GmbH) according to the manufacturer's instructions. 15 µg adenylated DNA was mixed with 10 mM azide-biotin solution. Cu-THPTA or Cu-TBTA was added to catalyze the cycloaddition.

The reactions were vortexed for 10 seconds and then incubated at 45° C. for 30 minutes at 100 rpm. Subsequently, biotinylated DNA was purified using AMPure XP beads. To prevent damage of DNA by copper ions, the biotinylated DNA was either washed six times with 70% EtOH or four times with 70% EtOH and two times with 70% EtOH+10 mM EDTA in order to complex the copper ions.

Finally, the biotinylated DNA was associated with magnetic streptavidin beads. Dynabeads™ M-280 streptavidin beads (Thermo Fisher Scientific) were washed using B&W buffer (10 mM Tris-HCl, pH 7.5, 1 mM EDTA, 2 M NaCl) three times. Dynabeads™ M-280 streptavidin beads were then mixed with 4.5 µg biotinylated DNA and incubated at 22° C. for 30 minutes at 1000 rpm. Afterwards the beads were centrifuged, put on magnet, and washed three times with 1× TE buffer.

In order to assess association efficiency, non-associated DNA in supernatant samples before and after association was digested using NsbI in the respective restriction buffer for 30 minutes at 37° C. and 850 rpm. Successful DNA digest would result in two DNA fragments of 1289 bp and 2586 bp. The restriction reaction was quantitatively analyzed using agarose gel electrophoresis (FIG. 7, lane 2 and 3).

Figure 7:
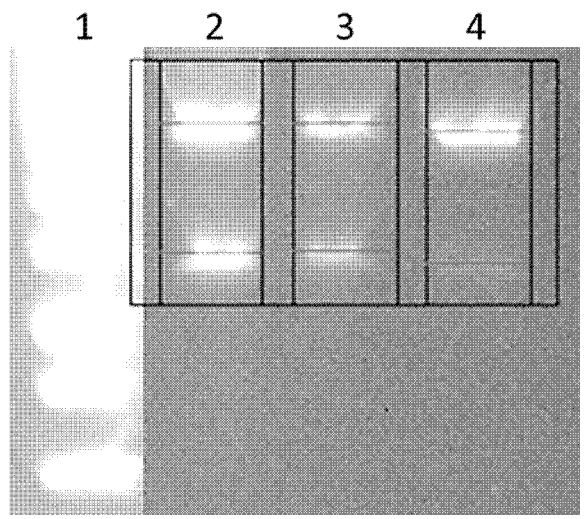
FIG. 7: Enzymatic Digest of Streptavidin-Associated DNA

When comparing lanes 2 and 3 of FIG. 7, it could be seen that the DNA quantity in the supernatant was less after the association reaction (lane 3 of FIG. 7). In fact, 70% of the biotinylated DNA could be associated to streptavidin magnetic beads.

In order to assess accessibility of enzymes to the streptavidin-associated DNA, said DNA was digested using NsbI in the respective restriction buffer for 30 minutes at 37° C. and 850 rpm. Successful DNA digestion this time would result in one DNA fragment of 2586 bp. The restriction reaction was quantitatively analyzed using agarose gel electrophoresis (FIG. 7, lane 4).

The result in FIG. 7, lane 4 shows that the streptavidin-associated DNA is still accessible to enzymatic reactions, namely to an enzymatic digestion.

Example 4: RNA In Vitro Transcription Using Streptavidin-Associated DNA

Having shown that the linearized DNA associated with streptavidin magnetic beads according to Example 3 was accessible to enzymatic digest, the present example was aimed at showing that the streptavidin-associated DNA is suitable as a template for run-off RNA in vitro RNA transcription.

Figure 8:
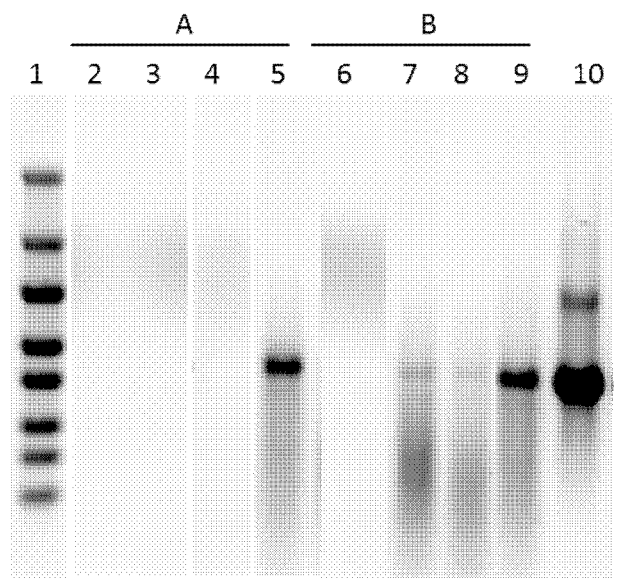
FIG. 8: RNA In Vitro Transcription Using Streptavidin-Associated DNA

During CuAAC, TBTA or THPTA (both copper stabilizing ligands) was used to stabilize the Cu(I)-catalysator for the cycloaddition. As a control for successful cycloaddition dATP instead of ethynyl-dATP was used (FIG. 8, lanes 2 and 6). In order to test whether complexation of copper ions via EDTA would improve RNA in vitro transcription and RNA quality, the coupling reaction with biotin was washed either six times with 70% EtOH (FIG. 8, lanes 3, 4, 7, 8) or four times with 70% EtOH and two times with 70% EtOH+10 mM EDTA (FIG. 8, lanes 5 and 9) before RNA in vitro transcription. In order to examine the influence of coupling of DNA, non-coupled linearized DNA was also used as a template for RNA production (FIG. 8, lane 10).

RNA in vitro transcription was performed as outlined in Example 1. The transcription reaction was stopped after 30 minutes by addition of 20 mM EDTA and RNA production was assessed by agarose gel electrophoresis (FIG. 8).

As shown in FIG. 8, streptavidin-associated DNA is a suitable template for in vitro transcription of RNA. Furthermore, it was found that the use of the water-soluble catalyst Cu(I)-THPTA (A) yields more RNA product than the use of Cu(I)-TBTA (B) (compare lanes 4, 5 as well as 8, 9 of FIG. 8). Moreover, it could be shown that complexation of copper ions with EDTA provides for high quality of the RNA product (compare lanes 4 and 5 and 8 and 9 of FIG. 8). Lane 10 of FIG. 8 shows a control of linear DNA without the coupling to biotin as a template for the RNA in vitro transcription.

Example 5: Improved RNA In Vitro Transcription Through Depletion of Copper Ions Via Stringent Washing The aim of this example was to find out whether stringent washing after the coupling reaction as described in Example 3 and before RNA in vitro transcription improves RNA quality. To this end, azide-biotin was coupled to linearized DNA via CuAAC using either Cu(I)-TBTA or Cu(I)-THPTA and washed either with 70% EtOH alone (wash I) or with 70% EtOH/10 mM EDTA (wash II). The washed biotinylated DNA was then associated with magnetic streptavidin beads as described in Example 4. The streptavidin bead-associated DNA was placed on a magnet, the supernatant was removed and the streptavidin bead-associated DNA was washed six times with wash buffer (0.5% Tween-20, 500 mM NaCl, 10 mM Tris, pH 8, 10 mM EDTA) (wash III) for 5 minutes at 22° C. and 850 rpm. Afterwards the beads were washed 3× with 1×TE buffer.

Figure 9:
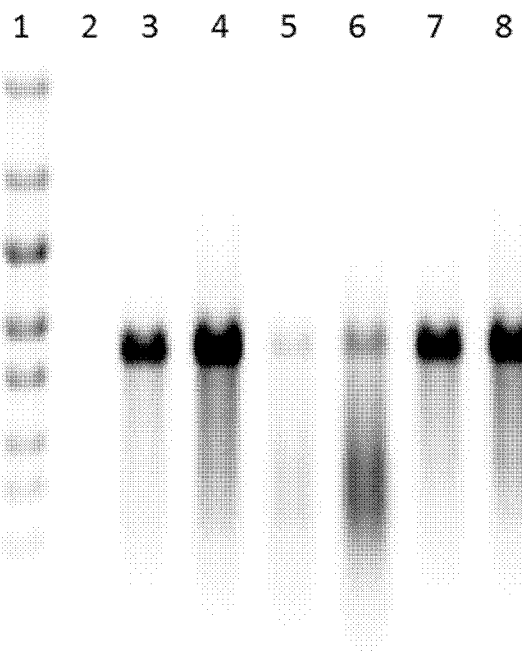
FIG. 9: In Vitro Transcription Using Different Washing Procedures

It was shown that efficiency and quality of RNA in vitro transcription from DNA associated with magnetic streptavidin beads is improved when washing with ethanol, wash I (see lanes 2 and 5 of FIG. 9) or ethanol and EDTA, wash II (see lanes 3, 7 of FIG. 9) and further washing with wash buffer, wash III (see lanes 4, 6 and 8 of FIG. 9). The improvement is most likely due to better DNA quality upon removal of Cu(I) ions.

Example 6: Coupling of Linearized Alkynated dsDNA to Azide Functionalized Magnetic Beads For all following examples 6.1. to 6.3., linearized alkynated dsDNA and magnetic beads functionalized with azide groups are used. Linearized alkynated dsDNA is obtained according to Example 3.

6.1. Cu-Free Cycloaddition:

1 µg alkynated dsDNA (resuspended in 50% DMSO and 50% WFI) is mixed with 500 µg magnetic azide beads overnight at room temperature and shaked at 1000 rpm. Following that, several washing steps are performed to remove unbound DNA and impurities as well as to prevent damage of nucleic acids by metal ions (3× wash with high salt buffer (0.5% Tween-20, 500 mM NaCl, 10 mM Tris pH 8.0, 10 mM EDTA), 3× wash with low salt buffer (0.5% Tween-20, 10 mM Tris pH 8.0, 10 mM EDTA) and 3× with 1× TE).

6.2. CuBr as Catalyst:

1 µg of alkynated dsDNA is mixed with 500 µg magnetic azide beads; Cu-THPTA or Cu-TBTA complexes (Catalyst) are added to catalyze the cycloaddition. The reactions are vortexed for 10 seconds and then incubated at RT overnight and shaked at 1000 rpm. Following that, several washing steps are performed to remove unbound DNA and impurities as well as to prevent damage of nucleic acids by any metal ions, i.e. Cupper (3× wash with high salt buffer (0.5% Tween-20, 500 mM NaCl, 10 mM Tris pH 8, 10 mM EDTA), 3× wash with low salt buffer (0.5% Tween-20, 10 mM Tris pH 8.0, 10 mM EDTA) and 3× wash with 1×TE buffer).

6.3. CuSO4 as Catalyst:

1 µg of alkynated dsDNA is mixed with 500 µg magnetic azide beads; CuSO4-THPTA with 20-70% DMSO and 10-70 mM Na-Ascorbate are added to catalyze the cycloaddition. The reactions were vortexed for 10 seconds and then incubated at RT for overnight and shaked at 1000 rpm. Following that, several washing steps are performed to remove unbound DNA and impurities as well as to prevent damage of nucleic acids by any metal ions, i.e. Cupper (3× wash with high salt buffer (0.5% Tween-20, 500 mM NaCl, 10 mM Tris pH 8.0, 10 mM EDTA), 3× wash with low salt buffer (0.5% Tween-20, 10 mM Tris pH8.0, 10 mM EDTA) and 3× with 1× TE buffer).

6.4. RNA In Vitro Transcription on Immobilized DNA:

The obtained DNA immobilized on magnetic beads (according to paragraph 6.1., 6.2, and 6.3.) is used in RNA in vitro transcription reactions.

Example 7: RNA In Vitro Transcription Using DNA Coupled at its 3' End of the Non-Coding Strand, DNA Coupled at its 3' End of the Coding Strand, or DNA Coupled at Both 3' Ends The aim of this example was to compare the results from RNA in vitro transcription reactions using linear DNA templates differing with respect to the positions of the coupled support.

7.1. Coupling of Linearized DNA to Azide-Biotin Via Cu(I)-Catalyzed Azide-Alkyne Cycloaddition (CuAAC) and Subsequent Association with Magnetic Streptavidin Beads:

1 mg of plasmid DNA (SEQ ID NO: 1) was linearized using 200 U NsbI for 2 h at 37° C. and 600 rpm to generate blunt DNA ends. Linearized DNA was purified using AMPure XP beads. Alkyne moieties which react to azide-biotin and enable association of the linearized DNA with streptavidin were generated by adenylating 300 µg of linearized DNA with 40 µM alkyne-dATP and 1 U Taq-polymerase for 55 min at 72° C. and 1000 rpm. The adenylation reaction was subsequently purified using AMPure XP beads.

Setting 1: Generation of DNA Coupled at its 3' of the Coding Strand

To obtain linear double stranded DNA with an alkyne-dATP only at the 3' end of the non-template strand (coding strand), the linearized adenylated DNA was digested with SspI for 60 min at 37° C. and 100 rpm and purified using AMPure XP beads. Cu(I)-catalyzed azide-alkyne cycloaddition of alkyne-dATP of the DNA with the azide group of an azide-biotin and association of biotinylated DNA with magnetic streptavidin beads (Dynabeads™ M-280) were essentially performed as described in Example 3. Obtained DNA beads were extensively washed as described in Example 5, and eventually used as template for RNA in vitro transcription (see 7.2).

Setting 2: Generation of DNA Coupled at its 3' of the Non-Coding Strand

To obtain linear double stranded DNA with an alkyne-dATP only at the 3' end of the template strand (non-coding strand), the linearized adenylated DNA was digested with AhdI for 60 min at 37° C. and 100 rpm and purified using AMPure XP beads. Cu(I)-catalyzed azide-alkyne cycloaddition of alkyne-dATP of the DNA with the azide group of an azide-biotin and association of biotinylated DNA with magnetic streptavidin beads (Dynabeads™ M-280) were essentially performed as described in Example 3. Obtained DNA beads were extensively washed as described in Example 5 and eventually used as template for RNA in vitro transcription (see 7.2).

Setting 3: Generation of DNA Coupled at Both 3' Ends

To obtain linear double stranded DNA with an alkyne-dATP at both 3' ends (i.e. at the 3' end of the non-template strand (coding strand) as well as at the 3' end of the template strand (non-coding strand)), the DNA purified after the adenylation reaction as described above was used. Cu(I)-catalyzed azide-alkyne cycloaddition of alkyne-dATP of the DNA with the azide group of an azide-biotin, and association of biotinylated DNA with magnetic streptavidin beads (Dynabeads™ M-280) was essentially performed as described in Example 3. DNA beads were extensively washed as described in Example 5 and eventually used as template for RNA in vitro transcription (see 7.2).

7.2 RNA In Vitro Transcription Using Different Templates of Streptavidin-Associated DNA RNA in vitro transcription was essentially performed as outlined in Example 1. Three different reactions were performed using DNA coupled at its 3' of the coding strand (setting 1), DNA coupled at its 3' of the non-coding strand (setting 2), or DNA coupled at both 3' ends (setting 3) as DNA template. The transcription reaction was stopped after 30 min by addition of 48 mM EDTA, and RNA production was assessed by agarose gel electrophoresis (2 µl of non-purified in RNA product each; see FIG. 10).

Figure 10:
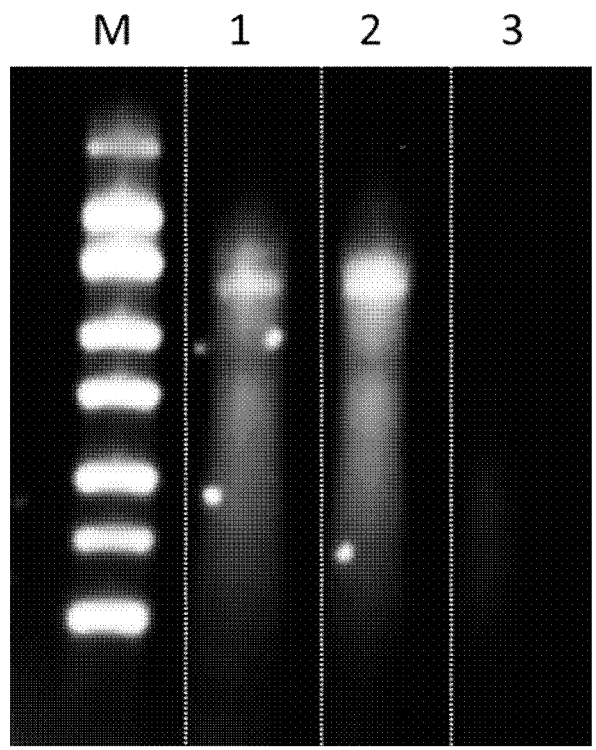
FIG. 10: RNA In Vitro Transcription of DNA Coupled at its 3' End of the Non-Coding Strand, DNA Coupled at its 3' End of the Coding Strand, or DNA Coupled at Both 3' Ends

As shown in FIG. 10, DNA immobilized at its 3' of the non-coding strand (Lane 2, FIG. 10) generates substantially more RNA during in vitro transcription reaction than DNA immobilized at its 3' of the coding strand (Lane 1, FIG. 10). Notably, no RNA was detectable on the agarose gel for reactions where DNA immobilized at both 3' ends was used (Lane 4, FIG. 10). The first lane, Lane M, corresponds to an RNA ladder.

The example shows that DNA coupled according to the invention (that is at the 3' end of its non-coding strand) is advantageous for the subsequent RNA in vitro transcription reaction. The results clearly show that the position of the support is crucial for RNA yield during RNA in vitro transcription. While not wishing to be bound by theory, the results seem to be explained by the fact that a support/bead on the 3' DNA end of the non-coding strand does not impair efficient run-off of the RNA polymerase (RNAP), while, in contrast, immobilization on the 3' DNA end of the coding strand may impair efficient run-off of the RNA polymerase, which would eventually reduce yield and/or quality of the produced RNA (see FIG. 1). As already shown in examples 1 and 2, the present example confirms that coupling on both ends results in DNA no longer accessible to enzymatic reactions.

SUMMARY OF THE EXAMPLES

It becomes apparent from the foregoing examples that a DNA, which was coupled to a tag such as biotin via CuAAC (see Examples 3 to 5 and 7) and also further associated with streptavidin via the biotin-tag is accessible to enzymatic reactions and is therefore e.g. suitable for use in RNA in vitro transcription reactions. When comparing the coupling to a tag/bead in terms of the strand, to which the tag/bead is coupled, the coupling at the 3' end of the non-coding strand provides for an increased yield and/or quality of the produced RNA when compared to the coupling at the 3' end of the coding strand (see Example 7). The afore-mentioned accessibility and suitability of the templates provided according to Examples 3 to 5 is surprising since templates generated in other ways (see Example 1 via CnBr or Example 2 via EDC/sulfo-NHS or Example 7 via BaseClick on both 3' ends) are not accessible to enzymatic reactions and can therefore not be used in e.g. RNA in vitro transcription reactions.

The invention claimed is:

1. A method for producing RNA in vitro comprising
(I) producing a linear double stranded DNA comprising the steps of:
(a) providing linear double stranded DNA comprising a coding strand and a non-coding strand, said coding strand comprising an RNA polymerase promotor sequence element and a coding sequence element followed by a restriction site element;
(b) incubating said DNA with (i) a modified deoxynucleotide and (ii) an enzyme capable of adding said modified deoxynucleotide at a 3' end of a strand in order to provide linear double stranded DNA with a modified deoxynucleotide at the 3' end of each strand;
(c) coupling the DNA obtained in step (b) via the modified deoxynucleotide at the 3' end of each strand to a support;
(d) incubating the DNA obtained in step (c) with a restriction endonuclease recognizing said restriction element in order to provide linear double stranded DNA, wherein the non-coding strand of said DNA is coupled at its 3' end to a support and wherein said support is the only support coupled to said DNA
(II) providing (i) ribonucleoside triphosphates and (ii) a DNA-dependent RNA polymerase; and
(III) incubating the DNA provided in step (I)(d) with (i) and (ii) provided in step (II) under suitable conditions in order to produce RNA.

2. The method according to claim 1, wherein the modified deoxynucleotide is selected from the group consisting of an alkyne deoxynucleotide, an azide deoxynucleotide, an azadibenzocyclooctyne deoxynucleotide, a trans-cyclooctene deoxynucleotide, and a vinyl deoxynucleotide.

3. The method according to claim 1, wherein the enzyme capable of adding a modified deoxynucleotide at the 3' end of a strand in step (b) is a DNA polymerase.

4. The method according to claim 1, wherein the DNA-dependent RNA polymerase is a bacteriophage RNA polymerase.

5. The method of claim 4, wherein the bacteriophage RNA polymerase is SP6 polymerase.

6. The method of claim 4, wherein the bacteriophage RNA polymerase is T7 polymerase.

7. The method of claim 4, wherein said non-coding strand is coupled at its 3' end to a support via a triazole.

8. The method according to claim 4, wherein said modified deoxynucleotide comprises biotin.

9. The method according to claim 8, wherein said biotin is associated with streptavidin.

10. The method according to claim 4, wherein the coding sequence element is flanked by a 5' UTR and/or a 3' UTR element.

11. The method of claim 10, wherein the linear double stranded DNA comprises (i) an RNA polymerase promotor sequence element; (ii) a 5' UTR sequence; (iii) the coding sequence element; (iv) a 3'UTR sequence; and (v) a poly-A sequence, followed at the 3' end by a restriction site element.

12. The method of claim 11, wherein the poly-A sequence is at 50 nucleotides in length.

13. The method according to claim 1, wherein a cap analogue is additionally provided in step (II).

14. The method according to claim 1, wherein a ribonuclease inhibitor is additionally provided in step (II).

15. The method according to claim 1, wherein pyrophosphatase is additionally provided in step (II).

16. The method according to claim 1, wherein $MgCl_2$ is additionally provided in step (II).

17. The method according to claim 1, wherein step (II) includes at least one ribonucleoside triphosphate analog.

18. The method according to claim 1, wherein the DNA provided in step (I)(d) is re-used in at least two further RNA in vitro production cycles, defined is steps (II) and (III).

19. The method according to claim 1, wherein the DNA provided in step (I)(d) is re-used in at least one further RNA in vitro production cycle, defined is steps (II) and (III).

* * * * *

```
                        SEQUENCE LISTING

<160> NUMBER OF SEQ ID NOS: 1

<210> SEQ ID NO 1
<211> LENGTH: 3907
<212> TYPE: DNA
<213> ORGANISM: Artificial Sequence
<220> FEATURE:
<223> OTHER INFORMATION: sequence of plasmid DNA

<400> SEQUENCE: 1
cagctgcatt aatgaatcgg ccaacgcgcg gggagaggcg gtttgcgtat tgggcgctct      60
tccgcttcct cgctcactga ctcgctgcgc tcggtcgttc ggctgcggcg agcggtatca     120
gctcactcaa aggcggtaat acggttatcc acagaatcag gggataacgc aggaaagaac     180
atgtgagcaa aaggccagca aaaggccagg aaccgtaaaa aggccgcgtt gctggcgttt     240
ttccataggc tccgcccccc tgacgagcat cacaaaaatc gacgctcaag tcagaggtgg     300
cgaaacccga caggactata aagataccag gcgtttcccc ctggaagctc cctcgtgcgc     360
tctcctgttc cgaccctgcc gcttaccgga tacctgtccg ccttctccc ttcgggaagc      420 gtggcgcttt ctcatagctc acgctgtagg tatctcagtt cggtgtaggt cgttcgctcc     480
aagctgggct gtgtgcacga accccccgtt cagcccgacc gctgcgcctt atccggtaac     540
tatcgtcttg agtccaaccc ggtaagacac gacttatcgc cactggcagc agccactggt     600
aacaggatta gcagagcgag gtatgtaggc ggtgctacag agttcttgaa gtggtggcct     660
aactacggct acactagaag aacagtattt ggtatctgcg ctctgctgaa gccagttacc     720
ttcggaaaaa gagttggtag ctcttgatcc ggcaaacaaa ccaccgctgg tagcggtggt     780 tttttgttt gcaagcagca gattacgcgc agaaaaaaag gatctcaaga agatcctttg      840
atcttttcta cggggtctga cgctcagtgg aacgaaaact cacgttaagg gattttggtc      900
atgagattat caaaaaggat cttcacctag atccttttaa attaaaaatg aagttttaaa      960
tcaatctaaa gtatatatga gtaaacttgg tctgacagtt accaatgctt aatcagtgag     1020
gcacctatct cagcgatctg tctatttcgt tcatccatag ttgcctgact ccccgtcgtg     1080
tagataacta cgatacggga gggcttacca tctggcccca gtgctgcaat gataccgcga     1140
gacccacgct caccggctcc agatttatca gcaataaacc agccagccgg aagggccgag     1200
cgcagaagtg gtcctgcaac tttatccgcc tccatccagt ctattaattg ttgccgggaa     1260
gctagagtaa gtagttcgcc agttaatagt ttgcgcaacg ttgttgccat tgctacaggc     1320
atcgtggtgt cacgctcgtc gtttggtatg gcttcattca gctccggttc caacgatca     1380
```

```
aggcgagtta catgatcccc catgttgtgc aaaaaagcgg ttagctcctt cggtcctccg    1440
atcgttgtca gaagtaagtt ggccgcagtg ttatcactca tggttatggc agcactgcat    1500
aattctctta ctgtcatgcc atccgtaaga tgcttttctg tgactggtga gtactcaacc    1560
aagtcattct gagaatagtg tatgcggcga ccgagttgct cttgcccggc gtcaatacgg    1620
gataataccg cgccacatag cagaacttta aaagtgctca tcattggaaa acgttcttcg    1680
gggcgaaaac tctcaaggat cttaccgctg ttgagatcca gttcgatgta acccactcgt    1740
gcacccaact gatcttcagc atctttact ttcaccagcg tttctgggtg agcaaaaaca    1800
ggaaggcaaa atgccgcaaa aaagggaata agggcgacac ggaaatgttg aatactcata    1860
ctcttccttt ttcaatatta ttgaagcatt tatcagggtt attgtctcat gagcggatac    1920
atatttgaat gtatttagaa aaataaacaa atagggttc cgcgcacatt tccccgaaaa    1980
gtgccacctg acgtctaata cgactcacta tagggagaaa gcttaccatg gaggacgcca    2040
agaacatcaa gaagggcccg cgcccttct acccgctgga ggacgggacc gccggcgagc    2100
agctccacaa ggccatgaag cggtacgccc tggtgccggg cacgatcgcc ttcaccgacg    2160
cccacatcga ggtcgacatc acctacgcgg agtacttcga gatgagcgtg cgcctggccg    2220
aggccatgaa gcggtacggc ctgaacacca accaccggat cgtggtgtgc tcggagaaca    2280
gcctgcagtt cttcatgccg gtgctgggcg ccctcttcat cggcgtggcc gtcgccccgg    2340
cgaacgacat ctacaacgag cgggagctgc tgaacagcat ggggatcagc cagccgaccg    2400
tggtgttcgt gagcaagaag ggcctgcaga agatcctgaa cgtgcagaag aagctgccca    2460
tcatccagaa gatcatcatc atggacagca agaccgacta ccagggcttc cagtcgatgt    2520
acacgttcgt gaccagccac ctcccgccgg gcttcaacga gtacgacttc gtcccggaga    2580
gcttcgaccg ggacaagacc atcgccctga tcatgaacag cagcggcagc accggcctgc    2640 cgaaggggt ggccctgccg caccggaccg cctgcgtgcg cttctcgcac gcccgggacc    2700
ccatcttcgg caaccagatc atcccggaca ccgccatcct gagcgtggtg ccgttccacc    2760
acggcttcgg catgttcacg accctgggct acctcatctg cggcttccgg gtggtcctga    2820
tgtaccggtt cgaggaggag ctgttcctgc ggagcctgca ggactacaag atccagagcg    2880
cgctgctcgt gccgacctg ttcagcttct tcgccaagag caccctgatc gacaagtacg    2940
acctgtcgaa cctgcacgag atcgccagcg ggggcgcccc gctgagcaag gaggtgggcg    3000
aggccgtggc caagcggttc cacctcccgg gcatccgcca gggctacggc ctgaccgaga    3060
ccacgagcgc gatcctgatc accccgagg gggacgacaa gccgggcgcc gtgggcaagg    3120
tggtcccgtt cttcgaggcc aaggtggtgg acctggacac cggcaagacc ctgggcgtga    3180
accagcgggg cgagctgtgc gtgcggggc cgatgatcat gagcggctac gtgaacaacc    3240
cggaggccac caacgccctc atcgacaagg acggctggct gcacagcggc gacatcgcct    3300
actgggacga ggacgagcac ttcttcatcg tcgaccggct gaagtcgctg atcaagtaca    3360
agggctacca ggtggcgccg ccgagctgg agagcatcct gctccagcac cccaacatct    3420
tcgacgccgg cgtggccggg ctgccggacg acgacgccgg cgagctgccg gccgcggtgg    3480
tggtgctgga gcacggcaag accatgacgg agaaggagat cgtcgactac gtggccagcc    3540
aggtgaccac cgccaagaag ctgcggggcg cgtggtgtt cgtggacgag gtcccgaagg    3600
gcctgaccgg gaagctcgac gcccggaaga tccgcgagat cctgatcaag gccaagaagg    3660
gcggcaagat cgccgtgtga ggactagtta taagactgac tagcccgatg gcctcccaa    3720
```

| | | | | |
|---|---|---|---|---|
| cgggccctcc | tcccctcctt | gcaccgagat | taataaaaaa aaaaaaaaaa | aaaaaaaaaa 3780 |
| aaaaaaaaaa | aaaaaaaaaa | aaaaaaaaaa | aaaaaaaatg | catccccccc cccccccccc 3840 |
| cccccccccc | ccccaaaggc | tcttttcaga | gccaccagaa | ttcggatact ctagacatat 3900 |
| gcttaag | | | | 3907 |